United States Patent
Jeney

(10) Patent No.: US 11,421,347 B2
(45) Date of Patent: *Aug. 23, 2022

(54) METHODS FOR LABELLING, ANALYZING, DETECTING AND MEASURING PROTEIN-PROTEIN INTERACTIONS

(71) Applicant: GENEVILLAGE KFT, Pilisszsetlászló (HU)

(72) Inventor: Csaba Jeney, Pilisszsetlászló (HU)

(73) Assignee: GENEVILLAGE KFT, Pilisszsetlászló (HU)

( * ) Notice: Subject to any disclaimer, the term of this patent is extended or adjusted under 35 U.S.C. 154(b) by 59 days.

This patent is subject to a terminal disclaimer.

(21) Appl. No.: 16/833,995

(22) Filed: Mar. 30, 2020

(65) Prior Publication Data

US 2021/0003585 A1    Jan. 7, 2021

Related U.S. Application Data

(62) Division of application No. 15/528,979, filed as application No. PCT/GB2015/053573 on Nov. 24, 2015, now Pat. No. 10,605,814.

(30) Foreign Application Priority Data

Nov. 24, 2014    (GB) .................................... 1420852

(51) Int. Cl.
| | |
|---|---|
| *C40B 30/04* | (2006.01) |
| *C12N 15/10* | (2006.01) |
| *G01N 33/68* | (2006.01) |
| *C12Q 1/6834* | (2018.01) |
| *C12Q 1/6872* | (2018.01) |
| *G01N 30/02* | (2006.01) |
| *C12Q 1/6853* | (2018.01) |
| *C12Q 1/686* | (2018.01) |

(52) U.S. Cl.
CPC .............. *C40B 30/04* (2013.01); *C12N 15/10* (2013.01); *C12N 15/101* (2013.01); *C12N 15/1037* (2013.01); *C12Q 1/6834* (2013.01); *C12Q 1/6872* (2013.01); *G01N 30/02* (2013.01); *G01N 33/68* (2013.01); *G01N 33/6845* (2013.01); *C12Q 1/686* (2013.01); *C12Q 1/6853* (2013.01); *G01N 2458/10* (2013.01); *G01N 2500/04* (2013.01)

(58) Field of Classification Search
None
See application file for complete search history.

(56) References Cited

FOREIGN PATENT DOCUMENTS

| WO | 2010097589 A1 | 9/2010 |
| WO | 2010135558 A1 | 11/2010 |

OTHER PUBLICATIONS

Bowley, Diana R. et al. "Libraries against libraries for combinatorial selection of replicating antigen-antibody pairs", Proceedings of the National Academy of Sciences, National Academy of Sciences, vol. 106, No. 5, Feb. 3, 2009, pp. 1380-1385.

(Continued)

*Primary Examiner* — Christian C Boesen
(74) *Attorney, Agent, or Firm* — . Meunier Carlin & Curfman LLC

(57) ABSTRACT

The present invention relates generally methods and kits for detecting binding interactions, in particular protein-protein interactions, and particularly to high throughput methods for labelling, analysing, detecting and measuring protein-protein interactions.

19 Claims, 2 Drawing Sheets

Specification includes a Sequence Listing.

(56) References Cited

OTHER PUBLICATIONS

D'Angelo, S. et al. "The anitbody mining toolbox", MABS, vol. 6, No. 1, Nov. 7, 2013, pp. 160-172.

D'Angelo, S. et al. "From deep sequencing to actual clones", Protein Engineering, Design and Selection, vol. 27, No. 10, Sep. 1, 2014, pp. 301-307.

Di Niro, R. et al. "Rapid interactome profiling by massing sequencing", Nucleic Acids Research, vol. 38, No. 9, Feb. 9, 2010, pp. e110-e110.

Gupta, Amita et al. "A Novel Helper Phage Enabling Construction of Genome-Scale ORF-Enriched Phage Display Libraries", PLOS One, vol. 8, No. 9, Sep. 27, 2013, pp. e75212.

Ivarsson, Y. et al. "Large-scale interaction profiling of PDZ domains through proteomic peptide-phage display using human and viral phage peptidomes" Proceedings of the National Academy of Sciences, vol. 111, No. 7, Feb. 3, 2014, pp. 2542-2547.

Larman, H. Benjamin et al. "Autoantigen discovery with a synthetic human peptidome", Nature Biotechnology, vol. 29, No. 6, May 22, 2011, pp. 535-541.

Li, Wei "ORF phage display to identify cellular proteins with different functions", Methods, vol. 58, No. 1, Sep. 1, 2012, pp. 2-9.

Ravn, U. et al. "By-passing in vitro screening—next generation sequencing technologies applied to antibody display and in silico candidate selection", Nucleic Acids Research, Information Retrieval Ltd, GB, vol. 38, No. 21, Jan. 1, 2010, pp. e193.1-e193.11.

Ravn, Ulla et al. "Deep sequencing of phage display libraries to support antibody discovery", Methods, vol. 60, No. 1, Mar. 1, 2013, pp. 99-110.

Sundell, Gustav N. et al. "Interaction Analysis through Proteomic Phage Display", Biomed Research International, vol. 11, No. 5, Sep. 11, 2014, pp. 499-9.

International Search Report and Written Opinion dated Feb. 3, 2016, from International Application No. PCT/GB2015/053573, 18 pages.

SEQUENCE LISTING

<160> NUMBER OF SEQ ID NOS: 31

<210> SEQ ID NO 1
<211> LENGTH: 20
<212> TYPE: DNA
<213> ORGANISM: Artificial Sequence
<220> FEATURE:
<223> OTHER INFORMATION: M13K07 Specific forward

<400> SEQUENCE: 1
ctcaagtcgg tgacggtgat                                              20

<210> SEQ ID NO 2
<211> LENGTH: 20
<212> TYPE: DNA
<213> ORGANISM: Artificial Sequence
<220> FEATURE:

<223> OTHER INFORMATION: M13KO7 Specific Reverse

<400> SEQUENCE: 2
gacaaaaggg cgacattcaa                                        20

<210> SEQ ID NO 3
<211> LENGTH: 20
<212> TYPE: DNA
<213> ORGANISM: Artificial Sequence
<220> FEATURE:
<223> OTHER INFORMATION: pBluescript II SK(+) specific forward

<400> SEQUENCE: 3
tcttgatccg gcaaacaaac                                        20

<210> SEQ ID NO 4
<211> LENGTH: 20
<212> TYPE: DNA
<213> ORGANISM: Artificial Sequence
<220> FEATURE:
<223> OTHER INFORMATION: pBluescript II SK(+) specific reverse

<400> SEQUENCE: 4
ttttctgcgc gtaatctgct                                        20

<210> SEQ ID NO 5
<211> LENGTH: 18
<212> TYPE: DNA
<213> ORGANISM: Artificial Sequence
<220> FEATURE:
<223> OTHER INFORMATION: pBluescript II SK(+) specific probe FAM-MGB
      labeled

<400> SEQUENCE: 5
ctggtagcgg tggttttt                                          18

<210> SEQ ID NO 6
<211> LENGTH: 20
<212> TYPE: DNA
<213> ORGANISM: Artificial Sequence
<220> FEATURE:
<223> OTHER INFORMATION: M13KO7 specific probe VIC-MGB labeled

<400> SEQUENCE: 6
ccgtcaatat ttaccttccc                                        20

<210> SEQ ID NO 7
<211> LENGTH: 40
<212> TYPE: DNA
<213> ORGANISM: Artificial Sequence
<220> FEATURE:
<223> OTHER INFORMATION: M13KO7 specific forward Primer

<400> SEQUENCE: 7
taacgtggga atggtgcttc ctcaagtcgg tgacggtgat                  40

<210> SEQ ID NO 8
<211> LENGTH: 20
<212> TYPE: DNA
<213> ORGANISM: Artificial Sequence
<220> FEATURE:
<223> OTHER INFORMATION: M13KO7 specific reverse primer

<400> SEQUENCE: 8
gacaaaaggg cgacattcaa                                        20

<210> SEQ ID NO 9
<211> LENGTH: 40
<212> TYPE: DNA
<213> ORGANISM: Artificial Sequence
<220> FEATURE:
<223> OTHER INFORMATION: pBluescript II SK(+) specific forward

<400> SEQUENCE: 9
gaagcaccat tcccacgtta tcttgatccg gcaaacaaac                    40

<210> SEQ ID NO 10
<211> LENGTH: 20
<212> TYPE: DNA
<213> ORGANISM: Artificial Sequence
<220> FEATURE:
<223> OTHER INFORMATION: pBluescript II SK(+) specific reverse

<400> SEQUENCE: 10
ttttctgcgc gtaatctgct                                          20

<210> SEQ ID NO 11
<211> LENGTH: 18
<212> TYPE: DNA
<213> ORGANISM: Artificial Sequence
<220> FEATURE:
<223> OTHER INFORMATION: pBluescript II SK(+) specific probe FAM-MGB
      labeled

<400> SEQUENCE: 11
ctggtagcgg tggttttt                                            18

<210> SEQ ID NO 12
<211> LENGTH: 20
<212> TYPE: DNA
<213> ORGANISM: Artificial Sequence
<220> FEATURE:
<223> OTHER INFORMATION: M13KO7 specific probe VIC-MGB labeled

<400> SEQUENCE: 12
ccgtcaatat ttaccttccc                                          20

<210> SEQ ID NO 13
<211> LENGTH: 20
<212> TYPE: DNA
<213> ORGANISM: Artificial Sequence
<220> FEATURE:
<223> OTHER INFORMATION: pBluescript II SK(+) specific reverse

<400> SEQUENCE: 13
ttttctgcgc gtaatctgct                                          20

<210> SEQ ID NO 14
<211> LENGTH: 20
<212> TYPE: DNA
<213> ORGANISM: Artificial Sequence
<220> FEATURE:
<223> OTHER INFORMATION: M13KO7 specific reverse

<400> SEQUENCE: 14
gacaaaaggg cgacattcaa                                          20

<210> SEQ ID NO 15
<211> LENGTH: 18
<212> TYPE: DNA
<213> ORGANISM: Artificial Sequence
<220> FEATURE:

```
<223> OTHER INFORMATION: pBluescript II SK(+) specific probe FAM-MGB
      labeled

<400> SEQUENCE: 15
ctggtagcgg tggttttt                                                       18

<210> SEQ ID NO 16
<211> LENGTH: 20
<212> TYPE: DNA
<213> ORGANISM: Artificial Sequence
<220> FEATURE:
<223> OTHER INFORMATION: M13KO7 specific probe VIC-MGB labeled

<400> SEQUENCE: 16
ccgtcaatat ttaccttccc                                                     20

<210> SEQ ID NO 17
<211> LENGTH: 22
<212> TYPE: DNA
<213> ORGANISM: Artificial Sequence
<220> FEATURE:
<223> OTHER INFORMATION: General Forward Primer

<400> SEQUENCE: 17
ccaagaacac gctgtatctg ca                                                  22

<210> SEQ ID NO 18
<211> LENGTH: 40
<212> TYPE: DNA
<213> ORGANISM: Artificial Sequence
<220> FEATURE:
<223> OTHER INFORMATION: Dimerisation capable general reverse primer

<400> SEQUENCE: 18
tgcgcatcca ttgtagaggt gagacggtga ccagggttcc                               40

<210> SEQ ID NO 19
<211> LENGTH: 40
<212> TYPE: DNA
<213> ORGANISM: Artificial Sequence
<220> FEATURE:
<223> OTHER INFORMATION: Dimerisation capable general reverse primer

<400> SEQUENCE: 19
acctctacaa tggatgcgca gagacggtga ccagggttcc                               40

<210> SEQ ID NO 20
<211> LENGTH: 21
<212> TYPE: DNA
<213> ORGANISM: Artificial Sequence
<220> FEATURE:
<223> OTHER INFORMATION: Dimer specific real-time forward primer

<400> SEQUENCE: 20
agttggagtc ttggggtcag g                                                   21

<210> SEQ ID NO 21
<211> LENGTH: 24
<212> TYPE: DNA
<213> ORGANISM: Artificial Sequence
<220> FEATURE:
<223> OTHER INFORMATION: Dimer specific real-time reverse primer

<400> SEQUENCE: 21
aggtgggtcg atgtttgact actg                                                24
```

```
<210> SEQ ID NO 22
<211> LENGTH: 19
<212> TYPE: DNA
<213> ORGANISM: Artificial Sequence
<220> FEATURE:
<223> OTHER INFORMATION: Dimer specific real-time PCR Probe

<400> SEQUENCE: 22
tctcacctct acaatggat                                                  19

<210> SEQ ID NO 23
<211> LENGTH: 17
<212> TYPE: DNA
<213> ORGANISM: Artificial Sequence
<220> FEATURE:
<223> OTHER INFORMATION: Anti-beta-galactosidase probe

<400> SEQUENCE: 23
gctagggcta tgtatcc                                                    17

<210> SEQ ID NO 24
<211> LENGTH: 19
<212> TYPE: DNA
<213> ORGANISM: Artificial Sequence
<220> FEATURE:
<223> OTHER INFORMATION: Anti-bovine ubiquitin PRobe

<400> SEQUENCE: 24
tgggtcgatg tttgactac                                                  19

<210> SEQ ID NO 25
<211> LENGTH: 22
<212> TYPE: DNA
<213> ORGANISM: Artificial Sequence
<220> FEATURE:
<223> OTHER INFORMATION: General forward Source BioScience (6001_hDAb)
      library specific primer

<400> SEQUENCE: 25
ccaagaacac gctgtatctg ca                                              22

<210> SEQ ID NO 26
<211> LENGTH: 40
<212> TYPE: DNA
<213> ORGANISM: Artificial Sequence
<220> FEATURE:
<223> OTHER INFORMATION: Dimerisation capable general reverse primer
      Source BioScience (6001_hDAb) library specific primer

<400> SEQUENCE: 26
tgcgcatcca ttgtagaggt gagacggtga ccagggttcc                           40

<210> SEQ ID NO 27
<211> LENGTH: 24
<212> TYPE: DNA
<213> ORGANISM: Artificial Sequence
<220> FEATURE:
<223> OTHER INFORMATION: General forward  PhD12 Phage Display Peptide
      Library specific primer

<400> SEQUENCE: 27
cgcaattcct ttagtggtac cttt                                            24

<210> SEQ ID NO 28
<211> LENGTH: 46
<212> TYPE: DNA
```

```
<213> ORGANISM: Artificial Sequence
<220> FEATURE:
<223> OTHER INFORMATION: Dimerisation capable general reverse primer
      PhD12 Phage Display Peptide Library specific

<400> SEQUENCE: 28
acctctacaa tggatgcgca tctgtatggg attttgctaa acaact                    46

<210> SEQ ID NO 29
<211> LENGTH: 24
<212> TYPE: DNA
<213> ORGANISM: Artificial Sequence
<220> FEATURE:
<223> OTHER INFORMATION: Dimer specific real-time forward primer

<400> SEQUENCE: 29
cggactgttg aaagttgttt agca                                            24

<210> SEQ ID NO 30
<211> LENGTH: 20
<212> TYPE: DNA
<213> ORGANISM: Artificial Sequence
<220> FEATURE:
<223> OTHER INFORMATION: Dimer specific real-time reverse primer

<400> SEQUENCE: 30
ggtcaccgtc tcacctctac                                                 20

<210> SEQ ID NO 31
<211> LENGTH: 17
<212> TYPE: DNA
<213> ORGANISM: Artificial Sequence
<220> FEATURE:
<223> OTHER INFORMATION: Dimer specific real-time probe

<400> SEQUENCE: 31
catacagatg cgcatcc                                                    17
```

METHODS FOR LABELLING, ANALYZING, DETECTING AND MEASURING PROTEIN-PROTEIN INTERACTIONS

CROSS-REFERENCE TO RELATED APPLICATIONS

This application is a continuation application of U.S. patent application Ser. No. 15/528,979, filed May 23, 2017, which is a National State Application filed under 35 U.S.C. § 371 of PCT/GB2015/053573 filed Nov. 24, 2015, which claims priority to United Kingdom Application No. 1420852.4 filed Nov. 24, 2014, the disclosures of which are incorporated herein by reference in its entireties.

FIELD OF THE INVENTION

The present invention relates generally methods and kits for detecting binding interactions, in particular protein-protein interactions, and particularly to high throughput methods for labelling, analysing, detecting and measuring protein-protein interactions.

BACKGROUND

Cellular architecture is defined by its complexes, the molecular machines that actually make a cell. Cell biology traditionally identifies proteins based on their individual actions as catalysts, signalling molecules, or building blocks of cells and microorganisms. Currently, we witness the emergence of a post-genomic view that expands the protein's role, regarding it as an element in a network of protein-protein interactions as well, with a 'contextual' or 'cellular' function within functional modules.

The qualitative and quantitative characterization of complex protein-protein networks and the identification of major cell type specific interacting proteins are paramount to understanding the physiological processes and alterations of protein-protein interactions in a multitude of human diseases such as cancer, autoimmune diseases and other disorders. Detailed insights in protein-protein networks and the identification of disease-associated differences may lead to new ways for the rational design and development of specific drugs. The pattern of protein-protein interactions in a cell or tissue may also be used as a tool for molecular diagnostics.

Proteins participate in complex interactions that represent the mechanistic foundation for much of the physiology and function of the cell. These protein-protein interactions are organized into exquisitely complex networks. The architecture of protein-protein interaction networks was proposed to be scale-free, with most of the proteins having only one or two connections but with relatively fewer 'hubs' possessing tens, hundreds or more links. The interaction networks are highly dynamic, allowing for rapid changes in the interactome, for example to external stimuli or even developmental processes.

Interactions between core proteins and between two or more module proteins are likely to be mediated by domain-domain interactions. Interactions within and between attachment proteins are less likely to occur in this manner. Despite the contribution of protein complexes and interactions to the regulation and execution of biological processes, relatively few complexes are well-understood in terms of structure and function.

Attempts to experimentally obtain kinetic constants for cellular interactions are sparse. These quantitative parameters will enable the development of differential equation-based kinetic models of cellular processes. Such models are necessary for the understanding of drug action and will promote the discovery of new drugs for many complex diseases. The development of quantitative multi-scale models can provide a theoretical understanding of the therapeutic action and adverse effects of drugs at a cellular level.

The term 'sampling' is used for experimental designs where only a subset of the population is interrogated. Representative sampling is not common in the generation of protein interaction datasets, where sampling has often been guided by biological priorities. The 'coverage' summarizes which part of the total set of possible interactions has actually been tested. In light of current technologies, it is not valid to make inferences about the 'interactome', e.g. the set of all physical interactions that take place in a cell under the conditions being studied.

Several methods have been devised to study protein-protein interaction including physical methods to select and detect proteins that bind another protein, such as protein affinity chromatography, affinity blotting, immunoprecipitation (including 2D gel electrophoresis and mass spectrometry), cross-linking; library-based methods: protein probing, phage display, two-hybrid system, other library-based methods and genetic methods: extragenic suppressors, synthetic lethal effects, overproduction phenotypes, overproduction of wild-type proteins and overproduction of mutant proteins; and unlinked non-complementation.

Many of these methods are not suited for high throughput protein-interaction analysis. The most promising high throughput technologies are available by the development of peptide- and protein-library screening techniques such as the yeast two-hybrid strategy, which is a method to identify and clone genes for proteins that interact with a protein of interest; two-hybrid arrays, where large-scale experiments are carried out in a colony-array format, in which each yeast colony expresses a defined pair of 'bait' and 'prey' proteins that can be scored for reporter gene activity—indicating interaction—in an automated manner; phage display where a library of proteins is panned against a "bait" protein and affinity-purification/mass-spectrometry (AP-MS), especially to define all complexes in the cell (the 'complexome') and their constituent proteins; and tandem affinity purification (TAP). TAP reveals interacting proteins as core, module, or attachment proteins, according to the frequency of their appearance in the various forms of that complex.

All of these methods have advantages and disadvantages related to the reliability, completeness and ease of information gained by using of these techniques. The ideal method captures the information of interactome in a time and cost effective manner, enabling random sampling and high redundancy of sampling. It provides dynamic, original cellular context based, native protein-protein interaction based, and comprehensive, sufficiently large coverage of quantitative interaction data of even large, multi-unit protein complexes. It suppresses the effects of random variables, such as detecting of non-specific, accidentally interacting proteins. It, also, diminishes the effect of variables, which are any binding event related variables involved in the detection principle other than the original protein-protein interaction.

Two-hybrid screens, especially the array based techniques, enable large scale interactome information generation. However there are major disadvantages due to their binary, pair wise detection, lack of the original context based dynamic information, artificial binding agent (hybrid proteins) and the yeast cellular context restricted principle (e.g. skewed post-translational modification compared to the original host). Almost all of these have been solved partly by various ways. However, a method, which combines all of these required features has not been devised.

Affinity based methods, especially those using mass spectrometry as the detection principle, generate a high amount of semi-quantitative interactome data, partly in the correct cellular context. However they are influenced by random and binding (affinity) related variables. They detect accidental, non-specific binding events. To generate a random sampled, high coverage, comprehensive dataset would require a significant amount of time and expense, which compromises the benefit of its potential to detect the dynamic nature of interactome. Some of these issues have been solved, especially using tandem affinity purification (TAP), where accidental, non-specific binding events are reduced to a minimum, however at the expense of less reliable protein-protein complex recovery.

These techniques have accelerated the generation of protein-protein interaction (PPI) data on a large scale. After the pioneering study on the interactome, several large-scale studies have been carried out resulting in some high quality datasets of pair wise protein-protein interactions. For instance, the filtered yeast interactome (FYI) is an intersection of different datasets, including Y2H data, AP-MS data, in silico predictions, Munich Information Centre for Protein Sequences physical interactions, and protein complexes reported in the literature.

As the existing methodological approaches do not fully meet the needs of protein-protein interaction and interactome studies, new methods for the analysis and characterizations of complex protein-protein networks are needed.

The present invention provides methods and kits for detecting binding interactions, in particular protein-protein interactions at the cellular level. The methods and kits can be used for simultaneously detecting all, or a subset of, interacting proteins in complex protein networks, preferably in the original context of cells. The methods and kits provide dynamic, original cellular context based, native protein-protein interaction based, and comprehensive, sufficiently large coverage of quantitative and potentially kinetic interaction data of even large, multi-unit protein complexes.

The invention can be used for detecting protein-protein interactions using antibody display technology, using a plurality of antibody phages as the binding agents. The invention can also be used for detecting protein-protein interactions using aptamer technology, using a plurality of aptamers as binding agents. The complexity of the plurality of binding agents can be varied in wide ranges between a few binding agents to tens of thousands or hundreds of thousands or millions or tens of millions or hundreds of millions of binding agents. To obtain low complexity binding agents from high complexity binding agents suitable for the invented method, a complexity reduction method is devised (enrichment).

More detailed interactions between target molecules can be identified and monitored. For example protein-protein interactions can be detected. The presence of two or more binding agents within a binding agent/target complex may indicate that two or more targets may be present within the complex. This indicates that the two or more targets may be interacting with, or bound to, each other. If an identifiable part of the specific binding agent is known, for example the protein or nucleic acid sequence, then the targets can be identified. This method can be carried out using highly parallel PCR amplification by linking the identifiable nucleic acid sequences of bound displayed antibody phages i.e. those with predetermined binding characteristics e.g. with known epitope sequences, or known to bind to a specific molecule. This can be done preferably by emulsion PCR. This may be carried out at low protein complex concentrations, preferably in compartments. The interactions between targets e.g. protein-protein interactions can be detected by highly parallel PCR amplification, preferably using reduced complexity binding detection agents. The target-target e.g. protein-protein interaction information is gained by sequencing of the linked identifiable sequences, preferably by highly parallel DNA sequencing or by other sequence detection means. Varying the amount of input material e.g. the target, can be used to collect ligand binding kinetics data. In addition the method can be carried out in the presence and absence of compounds to determine whether the compounds have any effect on the target interaction, and whether this effect is agonistic or antagonistic.

The invention can also use protein display technology, displaying protein fragments of an organism and determining the binding characteristics of a multitude of displayed antibodies, each antibody having unique identifiable sequence information and each displayed protein fragments having identifiable sequence information. Preferably the identifiable sequence information for the displayed protein fragments is the sequence encoding the displayed amino acid sequence. The identity of the bound antibodies can be determined from the identifiable sequence information for each antibody-protein complex. Optionally the identity of the bound protein fragment, within each antibody-protein complex can be identified. Optionally the identity of the bound antibodies and the identity of the bound protein fragment can be determined from the linked identifiable sequence information for each antibody-protein complex. The binding, kinetic characteristics can also be determined using different amounts of the target e.g. proteins and binding agents such as, displayed proteins or display antibodies.

The methods and compositions of the invention may also be used to identify compounds which may agonize or antagonize such protein-protein interactions. The present invention provides methods and kits for detecting binding interactions with antagonistic (disrupting) or agonistic (promoting) compounds. The invention provides methods and kits for simultaneously detecting the binding interactions of antagonistic and/or agonistic compounds in complex protein networks, preferably in the original context of cells. The methods and kits provide original cellular context based, native protein-protein interaction based data, which is comprehensive, and has sufficiently large coverage of both quantitative and, potentially, kinetic interaction data, even for large, multi-unit protein complexes.

SUMMARY OF THE INVENTION

The invention provides a method for determining a binding interaction between a binding agent and a target comprising a) contacting a binding agent library with a target to allow formation of binding agent/target complexes wherein each member of said binding agent library is associated with a unique nucleotide sequence;
b) separating said binding agent/target complexes;
c) linking the nucleotide sequence associated with the binding agent in the binding agent/target complex to form a linked nucleotide sequence;
d) identifying the binding agent present in the complex from the linked nucleotide sequence.

The present invention describes methods of analysing and characterizing complex binding interactions, in particular protein-protein networks or interactomes. The method is based on the co-localization related identification of binding agents and optionally their targets, such as proteins, where information on the co-localization of binding agents and optionally their targets, preferably in plurality of compartments, are pair wise linked and translated to a nucleotide. The identity of the binding agent and optionally the targets may also be determined from the nucleotide sequence. This information can be revealed by sequencing.

The present invention also describes methods of analysing and characterizing the effect of antagonistic (disrupting) or agonistic (promoting) compounds on target molecule interactions. The method is based on the identification of binding agents and their targets, such as proteins, in the presence and absence of the compound. The detection of complexes formed between the binding agents and their targets, and the identification of the binding agents is carried out, preferably in a plurality of compartments, by pair wise linkage of unique identification sequences of the bound target specific binding agents which are then translated to a nucleotide. The alteration of the quantity of complexes and the identity of the binding agents and optionally the target involved can be revealed by sequencing.

The binding agent is preferably an antibody, or an aptamer.

Preferably the binding agent is a member of an antibody display library or a library of antibodies wherein each antibody is labelled with said unique nucleotide sequence.

Preferably the target is also associated with a unique nucleotide sequence.

The nucleotide sequence associated with a binding agent in the complex can be linked to a second nucleotide sequence associated with a second binding agent in the complex. This method can be used to identify a plurality of binding agents which bind to a single target. For example when the target is a protein, the method can identify antibodies which bind to different epitopes on the protein. Alternatively the target can be a protein complex, and the method can identify a plurality of binding agents which bind to different proteins within the complex. For example the nucleotide sequence associated with one binding agent in the binding agent/target complex can be linked to a nucleotide sequence associated with a second binding agent in the binding agent/target complex. Once the identity of the binding agents is known (from the linked sequence), it may be possible to identify the components of the target, and thus, for example, the proteins in the target which naturally interact. For example if the binding agent is an antibody with known binding characteristics, the protein bound by the antibody may be identified. Thus the identity of the proteins within the target can be identified. This allows protein-protein interactions within the sample to be detected and identified. Furthermore once a protein-protein interaction has been identified, the method can be used to monitor the effect of a compound on the interaction.

Alternatively the nucleotide sequence associated with a binding agent in the binding agent/target complex can be linked to a nucleotide sequence associated with a target within the binding agent/target complex. This method can be used to identify which binding agent interacts with which target. For example it can be used to identify which members of a binding agent library can form a complex with a known target. This information can be used to characterise the members of a binding agent library to gain binding characteristics information.

Preferably, the production of said random paired, linked nucleic acid products comprises utilising at least two pairs of PCR primers to amplify identical or non-identical amplicons; wherein the PCR primers at 5' end have sequence tags wherein amplification with tagged primers results in random paired, linked nucleic acid products. More preferably, amplification is emulsion PCR amplification and the production of said amplicons and random paired, linked nucleic acid products are parallel processes.

Preferably, said sequencing of said joined amplification products is a highly parallel sequencing method.

The method of the present invention can be used to investigate the effect of a compound on the interaction between the binding agents and the targets or the interaction between two or more target molecules. The step of contacting the binding agent with a target can be carried out in the presence and absence of a compound, and results compared to determine whether the compound effects the binding interaction between the binding agent and the target or between the target molecules. This method can be utilised to identify potential pharmaceutical agents which can be used to treat medical diseases and conditions.

The invention also provides a kit for carrying out the method of the invention comprising
(i) A binding agent library wherein each member of said binding agent library is associated with a unique nucleotide sequence; and
(ii) a set of at least two pairs of primers for linking the nucleotide sequences associated with the binding agent; and optionally instructions for use.

The kit may further comprise a protein display library wherein each member of said library is associated with a unique nucleotide sequence.

DETAILED DESCRIPTION

The ideal method captures information from the interactome in a time and cost effective manner, enabling random sampling and high redundancy of sampling. The method provides comprehensive coverage of quantitative interaction data, even for large, multi-unit protein complexes. This data is obtained in an original cellular context so can measure native protein-protein interactions, and can used to detect dynamic interactions. The method suppresses the effects of random variables, such as detecting non-specific, accidentally interacting proteins. It also diminishes the effect of variables, which are any binding event related effect involved in the detection principle other than the original protein-protein interaction, for example self-binding or a specific binding.

Figure 1:
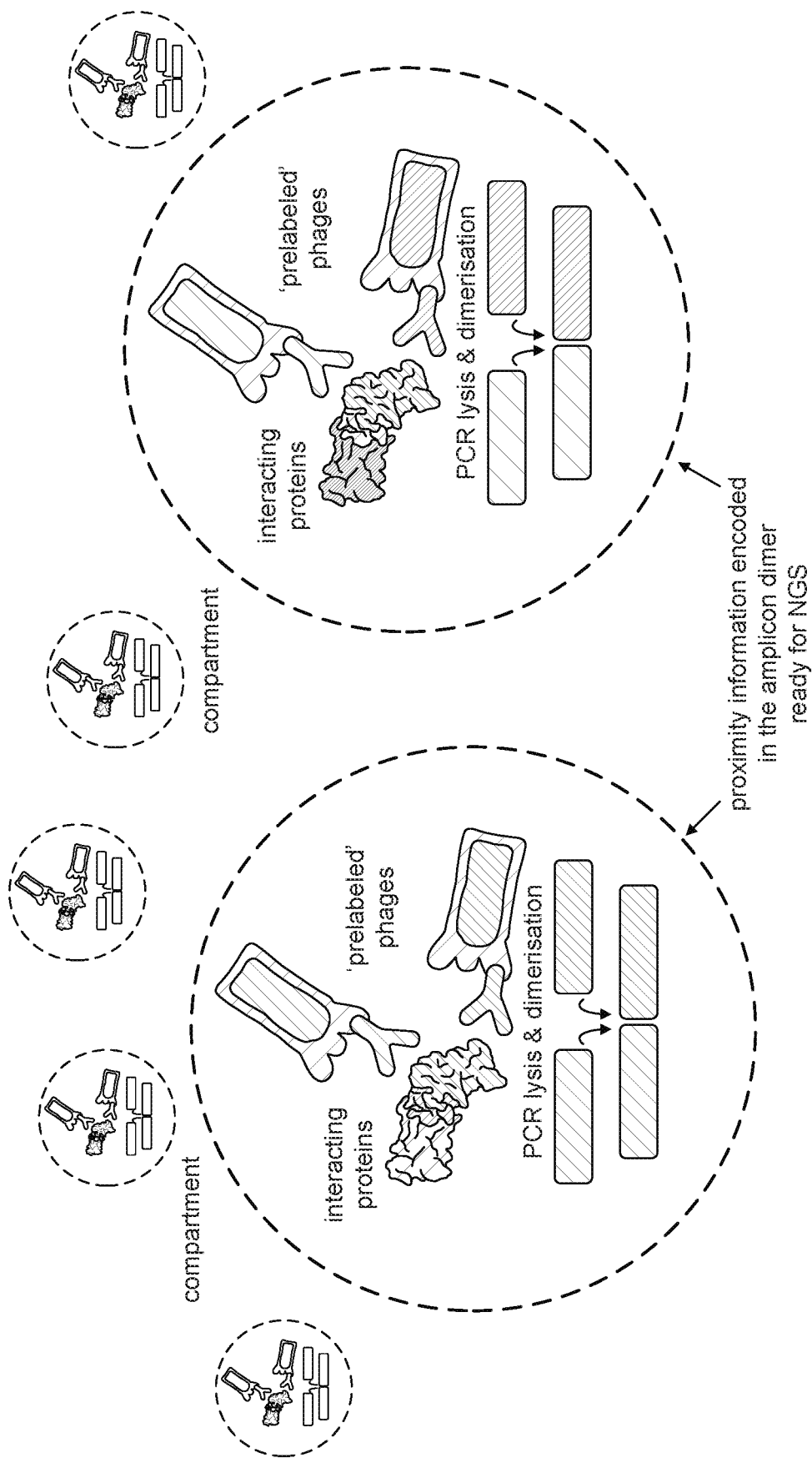
FIG. 1 depicts a general principle of the assay for detecting protein-protein interactions using methods and compositions of the present invention. Phages of an antibody library with predetermined binding characteristics information are used to reveal the binding information of interacting proteins. The binding information is determined in a plurality of compartments by PCR dimerization. The phages are lysed during the process releasing their unique DNA. These unique sequences are amplified using universal primers and dimerised. The dimerised products encoding the binding information is sequenced by next generation sequencing (NGS) and the bound protein identities are determined on the basis of the detection of specific, phages with known binding characteristics including the identities of its recognized binding targets.

One embodiment of the present invention is summarized in Figure. 1 and the different components of the assay system are described in detail below. A further embodiment of the present invention is summarized in Figure. 2 and the additional components of the system are described in detail below.

The invention provides a method for determining a binding interaction between a binding agent and a target comprising
  a) Contacting a binding agent library with a target to allow formation of binding agent/target complexes wherein each member of said binding agent library is associated with a unique nucleotide sequence;
  b) Separating said binding agent/target complexes;
  c) Linking the nucleotide sequences associated with the binding agents in the binding agent/target complex to form a linked nucleotide sequence;
  d) Identifying the binding agent present in the complex from the linked nucleotide sequence.

The method can be carried out ex vivo, in vivo or in vitro.

Binding Agent

Preferably the binding agent is an antibody, aptamer, or based on an engineered protein scaffold. Alternatively the binding agent may be a compound. The binding agent may be a member of an antibody display library or a library of antibodies wherein each antibody is labelled with a unique nucleotide sequence. The method may use displayed antibody agents as the binding agent, where the binding characteristics, for example, the target to which the binding agent binds is known and the unique nucleotide sequences associated with the plurality of displayed antibody agents are determined and the binding characteristics and unique nucleotide sequences are correlated with one another. Thus, the invention provides methods determining of the binding characteristics and relating these to the identifiable unique nucleotide sequence of the plurality of displayed antibody agents. This provides binding characteristic information.

The binding agent used in the invention may be an antibody. The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term "antibody" includes antibody fragments, derivatives, functional equivalents and homologues of antibodies, humanised antibodies, including any polypeptide comprising an immunoglobulin binding domain, whether natural or wholly or partially synthetic and any polypeptide or protein having a binding domain which is, or is homologous to, an antibody binding domain. Chimeric molecules comprising an immunoglobulin binding domain, or equivalent, fused to another polypeptide are therefore included. Cloning and expression of chimeric antibodies are described in EP-A-0120694 and EP-A-0125023. Examples of antibodies are the immunoglobulin isotypes (e.g., IgG, IgE, IgM, IgD and IgA) and their isotypic subclasses; fragments which comprise an antigen binding domain such as Fab, scFv, Fv, dAb, Fd; and diabodies. Antibodies may be polyclonal or monoclonal.

Complementarity determining regions (CDRs) are part of the variable chains in immunoglobulins (antibodies), generated by B-cells, where these molecules bind to their specific antigen. As the most variable parts of the molecules, CDRs are crucial to the diversity of antigen specificities generated by immunoglobulins. There are three CDRs (CDR1, CDR2 and CDR3), arranged non-consecutively, on the amino acid sequence of a variable domain of an immunoglobulin. Since the immunoglobulins are typically composed of two variable domains (on two different polypeptide chains, heavy and light chain), there are six CDRs for each antigen receptor that can collectively come into contact with the antigen.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., *Nature* 341:544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., *Science* 242:423-426 (1988); Huston et al., *PNAS USA* 85:5879-5883 (1988)); (viii) bispecific single chain Fv dimers (PCT/US92/09965) and (ix) "diabodies", multivalent or multispecific fragments constructed by gene fusion (WO94/13804; P. Hollinger et al., *Proc. Natl. Acad. Sci. USA* 90: 6444-6448 (1993)).

An "antigen binding domain" is the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains. An antigen binding domain may comprise an antibody light chain variable region (VL) and an antibody heavy chain variable region (VH).

Alternatively the binding agents may be based on engineered protein scaffolds. Protein scaffolds are derived from stable, soluble, natural protein structures which have been modified to provide a binding site for a target molecule of interest. Examples of engineered protein scaffolds include, but are not limited to, affibodies, which are based on the Z-domain of staphylococcal protein A that provides a binding interface on two of its a-helices (Nygren, P. A. (2008). FEBS J 275(11): 2668-76); anticalins, derived from lipocalins, that incorporate binding sites for small ligands at the open end of a beta-barrel fold (Skerra, A. (2008) FEBS J 275(11): 2677-83), nanobodies, and DARPins. Engineered protein scaffolds are typically targeted to bind the same antigenic proteins as antibodies. Short peptides may also be used to bind a target protein. Phylomers are natural structured peptides derived from bacterial genomes. Such peptides represent a diverse array of protein structural folds and can be used to inhibit/disrupt protein-protein interactions in vivo (Watt, P. M. (2006). Nat Biotechnol 24(2): 177-83)].

Alternatively, the binding agent may be an aptamer. Aptamers are synthetic oligonucleotides (DNA or RNA) that recognize target molecules with high affinity and specificity through a combination of shape complementarity and noncovalent chemical bonds (Blank & Blind, *Current Opin. Chem. Biol.,* 2005, 9:336-342). These artificial ligands are quite easy to obtain in vitro and can be developed to recognise a large variety of different molecule classes which range from mere ions (e.g. $Pb^{2+}$, Liu & Lu, 2003. *J Am Chem Soc.,* 125, 6642-6643) to nucleotides, small molecules, proteins, viruses, and cells up to whole organisms (Menger et al., 2006. *Handbook of Experimental Pharmacology,* 359-373). High binding affinity aptamers have been selected through the well-known SELEX method (Ellington & Szostak, 1990. *Nature,* 346, 818-822) for the detection of low molecular weight molecules like theophyllin (Jenison et al., 1994. *Science,* 263, 1425-1429), L-arginine (Geiger et al., 1996. *Nucl. Acids Res.,* 24, 1029-1036), moenomycin (Schuerer et al., 2001. *Bioorg. Med. Chem.,* 92, 2557-2563), 17b-estradiol (Kim et al., 2007. *Biosens. Bioelectron.,* 22, 2525-2531) but also for larger molecules like thrombin (thrombin-binding aptamer:5'-GGTTGGTGTGGTTGG-3' (SEQ ID NO: 32)) (Baldrich et al., *Anal Chem.* 2004, 76, 23, 7053-63), cholera toxin or HIV-1 tat protein, among others (for review see Tombelli et al., 2007, *Biomolec Eng.,* 24, 191-200). Some of the above mentioned aptamers have been used in ELISA-like assays on microplates or on the surface of biosensor transducers (QCM, SPR). An aptamer-modified AuNP colorimetric system has also been developed for the determination of the protein PDGF in a sandwich-based assay (Huang et al., 2005, 77, 5735-5741).

The binding agent may be part of a library, such as a displayed binding agent library, for example bacterial display, mRNA display, bacteriophage display, aptamer, ribosome display or yeast display libraries. Preferably the displayed binding agent library is an antibody bacteriophage display library. The library should be large enough so the library consists of a plurality of binding members which are expected to bind to at least 75% of the targets of interest within a target sample. More preferably the library is designed to bind to at least 80%, 85%, 90%, 95%, 97.5% or 99% of the targets of interest within a sample. For example the binding agent library comprises a plurality of binding members to protein or peptide sequences with 95% or higher coverage of expected or desired proteins within a sample. Such libraries are published in the literature. Each member of the library has a detectable, nucleic acid identity label, which is preferably unique to one member of the library. Preferably the unique nucleic acid identity labels are linked. "Linked" means the linking process has the potential to form random multimer nucleic acid products based on co-localization of these nucleic acid identity labels under suitable assay conditions. Preferably the multimeric product is a dimer. The suitable assay conditions include dismantling of bacteriophage particles, preferably in separate compartments, for example by heat treatment in lipid emulsion, and specific consensus amplification of the unique sequences produce linkable amplicons. The joining of the linkable amplicons e.g. binding display specific nucleic acid domains, form linked identity labels, which encodes the co-localisation information of the identity labels. Preferably the unique sequence is the binding display specific nucleic acid domains, for example the sequence which encodes one or more CDR regions. The joining reaction can be amplification based or involve other techniques. Amplification based joining can utilise two or more amplification primer pairs with identical binding abilities, but with complementary 5' tags or dimer linker sequences which result in the formation of polymerase extendable nucleic acid duplexes. The tags or dimer linker sequences mean that the sequence amplified by one primer pair will hybridise to sequences amplified by the second primer pair. The identity labels thereby become linked.

Each member of the binding agent library is associated with a unique nucleotide sequence, which can be used to identify the binding agent. "Associated" as used herein means that the presence of the binding agent in the complex can be detected by the presence of the nucleic acid sequence within the linked sequence generated in the method. The nucleotide sequence may be attached as a label to the binding agent, be part of the binding agent itself e.g. aptamer, or be present within the binding agent e.g. nucleic acid within a phage. For example each member of the library can be labelled with unique nucleotide sequence. As used herein "labelled" refers to a nucleotide sequence which is attached to the member of the library. Methods of attaching nucleotides to binding agents such as antibody or compounds are known in the art. Alternatively, if the binding agent library is a display library, as described above, the unique nucleotide sequence can be the sequence which encodes one or more CDR regions or the displayed binding domain. For example a display library can be generated by inserting sequences encoding the amino acid sequence to be displayed into a phage at a known location. Universal primers that will amplify the inserted sequences can then be used and thus identify the binding sequence. Alternatively if the binding agent is an aptamer, the aptamer itself can be the unique nucleotide sequence.

The nucleotide sequence is an oligonucleotide and may comprise RNA or DNA, single or double stranded. Nucleotides used to label the binding agent or target are generally 5-150 bases in length, for example 10-40, or 20-30 bases in length. The nucleotides that form the nucleic acid can be chemically modified to increase the stability of the molecule, to improve its bioavailability or to confer additional activity on it. For example the pyrimidine bases may be modified at the 6 or 8 positions, and purine bases at the 5 position with CH3 or halogens such as I, Br or Cl. Modifications or pyrimidines bases also include 2 $NH_3$, $O^6$—$CH_3$, $N^6$—$CH_3$ and $N^2$—$CH_3$. Modifications at the 2'position are sugar modifications and include typically a $NH_2$, F or $OCH_3$ group. Modifications can also include 3' and 5' modifications such as capping.

Alternatively modified nucleotides, such as morpholino nucleotides, locked nucleic acids (LNA) and peptide nucleic acids (PNA) can be used. Morpholino oligonucleotides are assembled from different morpholino subunits, each of which contains one of the four genetic bases (adenine, cytosine, guanine, and thymine) linked to a 6-membered morpholine ring. The subunits are joined by non-ionic phosphorodiamidate intersubunit linkages to give a morpholino oligonucleotide. LNA monomers are characterised in that the furanose ring conformation is restricted by a methylene linker that connects the 2'-O position to the 4'-C position. PNA is an analogue of DNA in which the backbone is a pseudopeptide rather than a sugar.

Preferably, the binding agents are capable of detecting more than one target, preferably with different apparent affinities. Alternatively, the binding agents are capable of detecting a single target using different epitopes or binding sites, preferably with different apparent affinities.

The binding characteristics of the members of the antibody phage library can be pre-determined. For example it can be determined which epitope is bound by the CDRs encoded and expressed binding agent (antibody) of the phage. This information can be associated with the unique nucleotide sequence which encodes the CDRs. Thus the epitope bound by the antibody expressed by the phage can be identified from the sequence of the unique nucleotide sequence. Once the epitope sequence present in the bound target is known, it may be possible to identify the protein or the group of proteins bound.

It may be possible to determine the binding characteristics of the members of the antibody phage library using unique nucleotide sequence labelled epitopes or unique nucleotide sequence labelled epitope libraries.

Target

"Target" as used herein is the molecule or group of molecules which forms a complex with the binding agent. The complex is usually formed under normal physiological conditions of the organism of interest.

Preferably the target comprises a protein. More preferably the target is part of a protein sample. The protein sample may comprise a protein display library, preferably wherein each member of said library is associated with a unique nucleotide sequence. Preferably the protein display library is a cDNA phage display library. Optionally the target may be cross-linked to other targets within a plurality of targets e.g. a protein sample. For example a protein within a sample may be cross-linked to one or more other proteins within the sample.

The target can be a known target. Binding agents which form a complex with the target can be identified, including compounds which interact with the target. Alternatively the target may be unknown, and the method of the invention is used to identify the target, or a plurality of target molecules which interact with one another.

The target may be associated with a unique nucleotide sequence. "Associated" means that the presence of the target within the binding agent/target complex can be detected by the presence of the nucleic acid sequence within the linked sequence generated by the method. The nucleotide sequence may be attached as a label to the target, or be present within the target e.g. nucleic acid within a phage. Alternatively the nucleotide sequence may be part of an aptamer known to bind to the target. The binding agent/target complexes can be contacted with the aptamers to enable the target present to be identified through linkage of the unique nucleotide sequences, including the aptamer.

The assay of the present invention can be applied to any protein sample. Proteins can be derived from any biological specimen including, but not limited to tissues, cytological specimens, body fluids, cell cultures or any other protein complex containing material. Body fluid samples include blood, saliva, urine, cerebrospinal fluid, or serum. Alternatively the sample can be generated by recombinant expression methods. Preparation of proteins from specimens can be performed using standard methods known in the art. The specimen can be chemically treated before the extraction, e.g. different fixative chemicals or crosslinking agents can be used (e.g. BS3—(bis(sulfosuccinimidyl)suberate). The protein sample can be crosslinked or not crosslinked. Alternatively, proteins can be produced, for example, by in vitro transcription-translation systems, or by recombinant expression systems. Depending on the experimental objective and the type of protein-protein interaction under investigation, proteins can be analysed either in their denatured or non-denatured form and/or crosslinked or not crosslinked form. The protein sample can be analysed in a plurality of conditions to collect information about the quantitative binding characteristics of plurality of protein-protein interactions. For example the concentration or amount of the binding agent can be varied to determine dissociation constants and other kinetic parameters.

The protein mixture can be preselected. For example, the protein mixture can be an enrichment of specific proteins e.g. proteins from a specific cellular location, from a specific cell type, of a similar size or electrostatic charge, proteins with similar binding properties, similar sequence characteristics, or similar functions e.g. enzymes (Current Protocols in Molecular Biology (2006) 20.0.1-20.0.6 CHAPTER 20 Analysis of Protein Interactions.). Preferably the specific proteins comprise phosphoproteins, membrane proteins or naturally, post-translational, artificially modified proteins. The proteins in the protein mixture of the method can be denatured or non-denatured and/or crosslinked or not crosslinked.

The protein may be in the form of a protein display library. Examples comprise bacterial display, mRNA display, bacteriophage display, and ribosome display and yeast display libraries. Preferably the protein display library is a protein bacteriophage display library, more preferably a cDNA phage display library. The library should be large enough so that it consists of a plurality of peptide or protein members with at least 70% coverage of the proteins expected to be detected by the method in a sample. More preferably the library is large enough to provide 75%, 80%, 85%, 90%, 95%, 97.5%, 99% or higher coverage of the proteins or peptides in a sample. Preferably the display library provides coverage of any suitable biological entity e.g. a tissue sample or whole organism, for example 95% or higher of protein coverage of any suitable biological entity. Such libraries are published in the literature (Danner S, Belasco J G. T7 phage display: a novel genetic selection system for cloning RNA-binding proteins from cDNA libraries. Proc Natl Acad Sci USA. 2001 Nov. 6; 98(23):12954-9. Epub 2001 Oct. 23. PubMed PMID: 11606722; PubMed Central PMCID: PMC60806.). Each member of the library is associated with a unique nucleotide sequence, i.e. each member has a unique detectable, nucleic acid identity labels. Preferably the unique nucleic acid identity labels are linked. "Linked" means the linking process has the potential to form random multimer nucleic acid products based on co-localization of these nucleic acid identity labels under suitable assay conditions. Preferably the multimeric product is a dimer. The suitable assay conditions include dismantling of bacteriophage particles, preferably in separate compartments, for example by heat treatment in lipid emulsion, and specific consensus amplification of the unique sequences produce linkable amplicons. The joining of the linkable amplicons e.g. binding display specific nucleic acid domains, form linked identity labels, which encodes the co-localisation information of the identity labels. The joining reaction can be amplification based or involve other techniques. Amplification based joining can utilise two or more amplification primer pairs with identical binding abilities, but with complementary 5' tags or dimer linker sequences which result in the formation of polymerase extendable nucleic acid duplexes. The tags or dimer linker sequences mean that the sequence amplified by one primer pair will hybridise to sequences amplified by the second primer pair. The identity labels thereby become linked.

Figure 2:
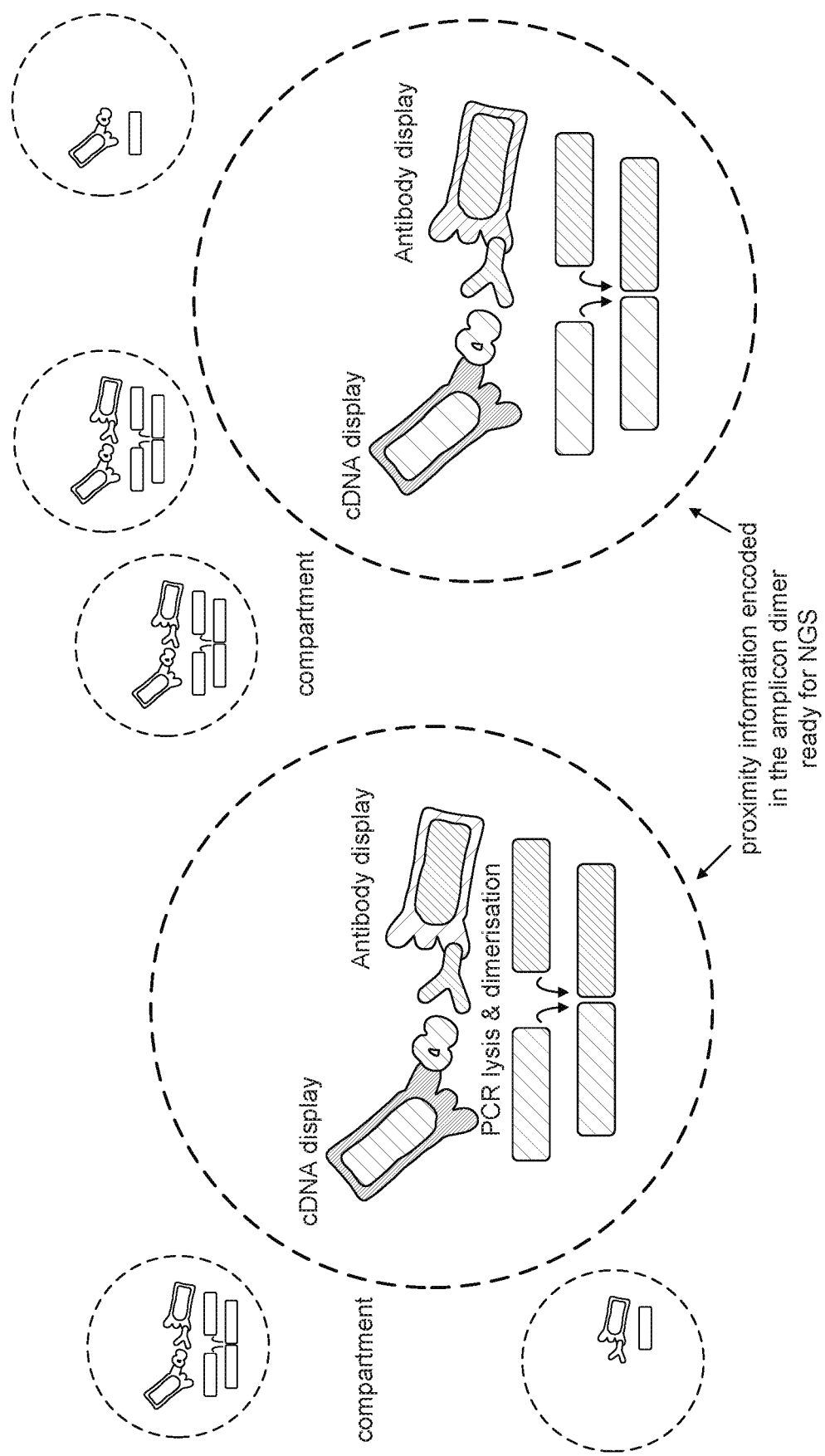
FIG. 2 depicts a general principle of the assay for characterization of a binding agent—to associate binding agent nucleic acid label identity to its binding characteristics information including the identity of its recognized binding targets using methods and compositions of the present invention. cDNA display and antibody display phages are bound to each other. The binding information is determined in a plurality of compartments by PCR dimerisation. The phages are lysed during the process releasing their unique DNA. These unique sequences are amplified using universal primers and dimerised. The dimerised products encoding the binding information is sequenced by next generation sequencing (NGS) and the protein identity of cDNA is determined from the sequence by database search and associated to binding agent nucleic acid label identity.

The identity labels i.e. the associated unique nucleotide sequences used in the binding agent library and target library, such as the protein display library and the antibody library, may be different in their biological background, and so the amplification and joining process is based on two different primer pairs, e.g. one primer pair amplifies target sequences such as cDNA based identity labels and the second primer pair amplifies binding agent specific nucleotide sequences used as identity labels. Joining of the different labels makes it possible to link binding agent specific information to target information e.g. proteins encoded by displayed cDNAs. An example of this process is shown in FIG. 2.

One binding agent, preferably a displayed antibody phage, can recognize a specific target e.g. a display protein target and the corresponding protein. This is termed specificity. Alternatively a plurality of binding agents may recognize one target, such as a specific target e.g. display protein and the corresponding protein. This is termed redundancy. Similarly one binding agent can recognize more than one target, such as a protein species, based on the similarity of the target conformation due to, for example, protein conformation or protein sequences. This phenomenon is termed cross-reactivity. Furthermore, binding agent recognition of a target protein is based on conformation of protein or its protein sequence. This is known as its reactivity. Protein binding affinities of binding agents such as displayed binding agents can be calculated from the quantitative information of the sequencing datasets. The predetermined binding characteristics of the members of displayed binding agents may include reactivity and cross-reactivity with specificity and redundancy with calculated affinities.

One can use these measures to calculate the detected target-target e.g. protein-protein interactions. By calculation based on inputs of reactivity, specificity and redundancy and the identities and abundance of linked identity labels one gains insight of specific target-target e.g. protein-protein interactions. Similarly, using these measures one can diminish the uncertainty of calculations induced by cross-reactivity, wherein redundancy and affinities of displayed antibody agents are taken into account. A varied concentration of the binding agent and/or target can be used to calculate quantitative parameters for the plurality of interactions, such as protein-protein interactions. Thus preferably the method is carried out using different concentrations of the binding agent and/or target.

The quantitative nature of the detection enables the determination and calculation of the background, non-informative sequencing reads, produced by the non-specific co-localisation of identity labels or self-linking of the same identity labels. However the detection of self-linking labels contains information about the quality of the datasets.

To achieve sufficient coverage, enriched libraries can be used. Both the binding agent library and/or the target library can be enriched. The displayed targets, such as the proteins can be enriched to cover all potential binding partners in the experimental context. Similarly, the displayed binding agents can be selected to have binding specificities enriched toward the detectable targets in the experimental context. For example, the library may be limited to specific targets of interest. This may be done by panning based selection e.g. a target sample with controlled complexity is immobilised on solid surface and contacted to the binding agent library selecting the bound agents of the binding agent library by washing and subsequent elution of bound agents. Similarly, a binding agent sample with controlled complexity is immobilised on solid surface and contacted to the target library selecting the bound targets of the target library by washing and subsequent elution of bound targets.

Preferably enrichment means the removal of self-binding displayed binding agents i.e. removal of binding agents which bind to other binding agents under assay conditions. More preferably enrichment means reducing the complexity of the displayed binding agent libraries, but still ensuring it has high coverage for detection of targets in the experimental context. Reducing the complexity may involve reducing the total number of member within the library, eliminating members which bind to non-target proteins, or selecting only those members which bind to a target of interest.

A binding agent library can be enriched by obtaining a protein mixture with components of interest e.g. studying known protein-protein interactions and validating dynamically their interactions or testing the effect of agonistic or antagonistic compounds. For example, immobilizing a target of interest e.g. protein mixture on a solid surface allows binding of the members of a binding agent library to the desired target e.g. protein. The binding agents bound to the target of interest can be separated from the unbound binding agents by dilution or other means. Bound members of the binding agent library can be eluted and used, as a reduced complexity library as described above, in the method of the invention.

Using enriched binding agent libraries is generally advantageous as the separation methods (for example microarrays or emulsion based separations) have limited capacity to produce individual complexes within one compartment, so that linked identifiable sequences can be obtained. The reduced complexity of an enriched display agent libraries is directly translatable to the number of the separations that need to be carried out to obtain separation based, random paired, joined amplification products.

Binding of Binding Agents

The method of the invention is preferably carried out under physiological conditions so that the interactions can be detected in their original context i.e. in the same conditions as present in the cell. This provides information on the binding interactions that occur naturally.

The step of contacting the binding agent library with the target is usually carried out in known buffer systems, from example in buffer systems that have already been used for studies of protein-protein interactions (e.g. TBST-buffer). Depending on the affinity, the reaction can be carried out at room temperature or 4° C. To get reproducible signals optimal time, optimal temperature and other assay conditions are determined including the steps of binding, washing and detection. Optimal conditions can be determined by the person skilled in the art.

Separating of Protein Complexes with the Bound Displayed Antibody Agents

The binding agent/target complexes need to be separated, i.e. isolated from other complexes prior to linking the label sequences i.e. the associated unique nucleotide sequences. The separation is carried out by methods known in the art. For example separation can be carried out by dilution, specific binding, or separation by physical and/or chemical properties. Preferably, the complexes are separated into compartments, such as emulsion droplets, micro-cavities etc., preferably diffusion limited or separated compartments.

Preferably, said separation comprises any one or more of solid surface binding, dilution or phase separation among the others, or providing diffusion limited or separated compartments. The separation limits the number of unbound binding agents in a compartment, preferably to one, on average. For example, the mean number of unbound binding agents in a compartment is one. The compartments may be individual droplets within an emulsion, or individual physical chambers such as microcavities. The complexes may be separated according to physical or chemical characteristics. Preferably, said dilution is limited dilution.

The compartmentalization (e.g. effective separation or isolation of large number reactions) is based on the Poisson distribution based separation of single unbound phages; e.g. emulsions and microarray are the best known state-of-art method.

Separating the binding agent/target complexes sufficiently prior to further analysis will provide the circumstances where pairs of nucleic acid labels are generated, which are based on co-localization of binding agents. If the complexes are not separated sufficiently nucleic acid labels from members of different complexes will become linked and thus provide false information. Separation reduces the amount of non-specific co-localisations of nucleic acid identity labels and allows the identification of specific binding partners especially when complex protein mixtures are investigated. For example separation may result, on average, in a single unbound binding agent per compartment, where linking will provide only self-linked nucleotide sequences, consequently reducing the possibility of random linking between the members of the binding agent library. As the distribution of any agents is based on Poisson distribution the necessary measures to achieve suitable separation of agents can be calculated. This preferably results in a single complex within one compartment. Preferably, an emulsion is used, which can be utilised in the amplification and linking of specific nucleic acid domains to form linked identity labels. Emulsion amplification methods are well known to the person skilled in the art, for example Schütze et al., Anal. Biochem. 2011 Mar. 1; 410 (1):155-7.

Solid Surface for Immobilization

Optionally the binding agent/target complex is immobilised following separation. For example the binding agent/target complexes can be captured onto a surface, for example as part of an array. This can help to maintain the separation between the complexes. Preferably separation of the complexes is maintained, for example, during the linking step.

The binding agent/target complexes are optionally immobilized on solid support surfaces, including, but not limited to, membranes e.g. polyvinylidene fluoride (PVDF) or nitrocellulose, plastic surfaces (e.g. polystyrene) or can be covalently coupled to appropriate beads (e.g. Epoxy-activated beads). The binding or coupling to solid surfaces is performed by standard methods for proteins ("Antibodies, a Laboratory Manual." Harlow, E., and Lane, D., eds. Cold Spring Harbor Press, Cold Spring Harbor N.Y., 1988) or by specific binding including antibodies or other specific binding interaction e.g. biotin-avidin.

The immobilization may comprise (a) obtaining solid support with universal recognized protein complex binding ability i.e. the solid support is capable of binding all members of the binding agent library or target molecules. The amount of the recognized protein complexes and the number of available binding sites on the solid support should be balanced so as to achieve sufficient separation between bound recognized protein complexes. Preferably, said solid support comprises a membrane, a plastic surface, or a bead. More preferably, the solid support is a bead and separation is achieved wherein on average one binding agent/target complex is bound to one bead. More preferably, the universal recognized protein complex binding ability is provided by an anti-bacteriophage antibody. Preferably, separation comprises physical separation in reaction chambers or physical-chemical separation in droplets within an emulsion.

Preferably, the production of said random paired, linked nucleic acid products comprises utilising at least two pairs of PCR primers to amplify identical or non-identical amplicons; wherein the PCR primers at 5' end have sequence tags wherein amplification with tagged primers results in random paired, linked nucleic acid products. More preferably, amplification is emulsion PCR amplification and the production of said amplicons and random paired, linked nucleic acid products are parallel processes. Preferably, said sequencing of said joined amplification products is a highly parallel sequencing method. Separation allows the specific formation of linked identity labels, wherein molecule that are co-localized in separated or diffusion limited compartments (e.g. on solid surface, in emulsion) have the propensity to specifically link the identity labels sequences of only the bound binding agents. However, the identity labels of unbound, but accidentally co-localized binding agents may also be linked. Similarly the identity labels from binding agents which are not bound within a complex can be linked. The linking process can provide a linked identity label with two identical identity labels e.g. where only one binding agent is present in the compartment. Similarly in the case of more than one binding agent recognizing a target, different linked identity labels can be produced with the same binding specificities. The linking step joins the identity label of one or more members of the binding agent library present. In addition the linking step may join the identity label of a member of a binding agent library to a nucleic acid sequence associated with the target. The linking process does not rely on the nucleic acids interacting with each other due to their close proximity e.g. by hybridising with each other. The sequences are joined together by using a linking process e.g. by amplification methods as described herein. The use of these methods, instead of relying on close physical proximity ligation assays, such as those in U.S. Pat. No. 7,306,904, allows multiple interactions to be detected in parallel. The labels do not need to be in close proximity to be linked and so detected. They simply need to be within the same compartment.

Linkage of Nucleotide Sequences

The unique nucleotide sequences associated with members of the complex can be linked by a method comprising:
(i) Amplifying the nucleotide sequence associated with the binding agents, and optionally if present the sequence associated with the target, using at least two pairs of PCR primers to produce at least two sets of amplicons, wherein the primers are designed so that the amplicons of the first set comprise a sequence, which is complementary to a sequence in the second set of amplicons;
(ii) Annealing the at least two sets of amplicons; and
(iii) Carrying out an amplification reaction to produce a linked nucleotide sequence Steps i-iii can be carried out sequentially or concurrently.

Each pair of primers comprises a forward primer and a reverse primer. The sequences of these primers are designed so that they allow amplification of the identifiable sequences. Preferably these are universal primers i.e. they bind to all of the identifiable sequence within a library e.g. all the members of a binding agent library, or target library. The sequence between the primers which is amplified is unique to one member of the library, allowing identification. Preferably the pairs of PCR primers are designed to produce a dimerised linked nucleic acid sequence, otherwise multimer linked nucleic acid sequence is produced. This is achieved by having dimer linker sequences at the 5' end of at least two primers amplifying the member amplicons of the dimer or the multimer. Thus these amplicons can form partially overlapping and polymerase extendable hybridisation products at their 3' ends. (for example as shown in FIG. 2)

Preferably the amplification is emulsion PCR amplification with suitable separation of the nucleotide sequences associated with the binding agents, or binding agent and target.

Optionally the linked nucleotide sequences from more than one complex are combined prior to identifying the linked binding agents and/or targets present. The identity of the binding agent(s) and/or target(s) can be determined, for example, by sequencing the linked nucleotide sequences. This can be carried out using a highly parallel system. The linked sequences can be combined so that a single reaction can be carried out to identify all the linked sequences. For example all of the linked nucleotides can be sequenced in a single reaction. The linked sequences can be determined quantitatively, to measure the relative abundances of the linked sequences.

Determining the Information of Said Linked Nucleic Acid Products

Based on predetermined binding characteristics of the binding agents, the co-localization information can be inferred from the linked identity label. The plurality of linked identity labels i.e. unique nucleotide sequences associated with the binding agent and optionally the target, in the form of the counts of sequencing reads, provides information of the identities of the members of binding agent/target complexes and their relative abundance. Other information is also inferable, wherein information of all linked identity labels is taken into account. Examples include but are not limited to, comparing relative affinities to predetermined affinities of the binding agents, comparing relative abundances calculated for different binding agents, determination of bound and not bound target or protein ratios.

Based on the multimer PCR linking of CDR regions (CDR1, CDR2 and CDR3) of antibody binding agents, the sequence of all CDR regions can be determined using NGS sequencing. As the predetermined binding characteristics of the binding agents are, preferably, based on a single CDR region sequence identity, in one preferred embodiment, the full sequence information of antibody binding agents can be associated with its predetermined binding characteristics.

Determining the Effects of Compound on Plurality of Protein-Protein Interactions.

The method of the invention can comprise the step of contacting the binding agent library with a target in the presence or absence of a compound; to determine whether said compound effects the binding interaction. This method can be used to determine the effects of a compound or other chemical moieties on a plurality of binding interactions, for example protein-protein interactions. Preferably the method is used to detect compounds or chemical moieties which can promote or disrupt certain protein-protein or other detectable interactions wherein the compounds or chemical moieties act as drugs or eliminate or suppress the pathological consequences of such situations. Preferably, such drugs can be used to treat different disease including, but not limited to, cancer, infectious diseases, autoimmune diseases and others.

A compound as used herein refers to two or more atoms which are connected by covalent bonds. A chemical moiety is part of a compound, which forms a functional group. The compound may be a known pharmaceutical agent.

The method of the invention can comprise the step of contacting the binding agent library with a target in the presence or absence of a compound; to determine whether said compound effects the binding interactions.

In a further embodiment the invention provides methods to determine interactome data. In a plurality of compartments, binding agents, such as the displayed antibody agents are co-localized according to their binding characteristics i.e. two or more binding agents are present within one compartment as they bind the same target, or bind to targets which themselves interact or are bound to one another. Their identifiable sequences i.e. unique nucleotide sequences are linked carrying the co-localization information in the form of linked identities. On the basis of the binding characteristics information and co-localization information, information on both the protein-protein interactions and identities of proteins can be determined.

The invention also describes a method for determining protein-protein interaction in a specimen obtained comprising:
(a) obtaining a protein mixture;
(b) contacting a binding agent library with said protein mixture so that binding agent-protein complexes form, wherein each member of the binding agent library associated with a unique nucleotide sequence;
(c) separating said binding agent-protein complexes;
(d) optionally immobilizing said binding agent protein complexes on a solid surface;
(e) detecting said unique nucleotide sequence of said binding agents within said binding agent-protein complexes and linking said unique nucleotide sequence of said binding agents to provide linked nucleic acid products based on the co-localization provided by said separation
(f) optionally combining said linked nucleic acid products; and
(g) sequencing said linked nucleic acid products corresponding protein binding characteristics of said displayed antibody agents. The sequence of the linked nucleic acid products is used to infer the presence of a protein-protein interaction in said protein mixture in said specimen. The unique nucleotide sequence allows the antibody agent present to be identified, and the corresponding protein binding characteristics of said displayed antibody agents.

The protein-protein interaction data can be validated by statistical means, including background determination and subtraction of level of protein-protein interactions, determination of apparent relative affinities and relative abundances of proteins and protein-protein interactions.

The invention also relates to a method for determining the effects of a compound on protein-protein interaction present in a specimen comprising:
(a) obtaining a protein mixture in the presence and absence of a compound;
(b) contacting a binding agent library with said protein mixture so that binding agent-protein complexes form wherein each member of the binding agent library is associated with a unique nucleotide sequence;
(c) separating said binding agent-protein complexes;
(d) optionally immobilizing said binding agent protein complexes on solid surface;
(e) detecting said unique nucleotide sequence associated with said binding agents within said binding agent-protein complexes and linking said unique nucleotide sequence associated with said binding agents to provide random paired, linked nucleic acid products based on the co-localization provided by said separation
(f) optionally combining said linked nucleic acid products; and
(g) sequencing said linked nucleic acid products
(h) comparing the information gained in the presence and absence of a compound;

The unique nucleotide sequence of the binding agent allows the binding agent present to be identified, and so the predetermined protein binding characteristics of said binding agents is used to infer the presence of a protein-protein interaction in said protein mixture in said specimen.

Preferably, the determination of the effect of the compound is determined using high throughput experimental setup.

In a further embodiment of the invention, there is provided a method for determining protein binding characteristics of the members of a binding agent library comprising:
(a) obtaining a displayed protein library wherein each member is associated with a unique nucleotide sequence;
(b) contacting a binding agent library with said displayed protein library to allow the formation of binding agent/protein complexes wherein each member of said binding agent library associated with a unique nucleotide sequence;
(c) separating said binding agent/protein complexes;
(d) optionally immobilizing said separated binding agent/protein complexes on a solid surface;
(e) linking the unique nucleotide sequences associated with the binding agents and the proteins to produce a linked nucleic acid product; optionally while maintaining separation of the complexes,
(f) optionally combining of the linked nucleic acid products;
(g) determining the sequence of the linked nucleic acid products.

The protein binding characteristics of the members of the binding agent library can be determined from the information within the sequence linked nucleic acid products. Detection of linked unique nucleotide sequence associated with the members of displayed agent libraries and the protein indicates recognition and binding to certain members of the displayed protein library. The sequence can provide information as to which members of the library bind to which proteins.

The protein binding characteristics of a plurality of said binding agents can be calculated. All the binding characteristics information for all members of said binding agent library can be combined, as binding information.

The linking of said unique nucleotide sequence associated with said binding agents and said proteins providing random paired, linked nucleic acid products based on the co-localization provided by said separation.

Preferably, the said binding agent libraries and/or targets (e.g. protein samples) are used in varied concentration in plurality of measurements to allow calculation of quantitative binding information including dissociation constants of said plurality of protein-protein interactions. The methods to calculate these measures are known to the person skilled in the art.

The invention also relates to kits for carrying out the methods of the invention. The kit comprises
a) a binding agent library wherein each member of said binding agent library is associated with a unique nucleotide sequence; and
b) a set of at least two pairs of primers for linking the nucleotide sequences associated with the binding agent; and optionally instructions for use.

The kit may also comprise a means for detecting protein-protein interactions wherein reagents, and optionally materials are provided to carry out any one or more of the following steps: separation, immobilization, detecting unique nucleotide sequences, linking of nucleotide sequences, and/or detecting linked nucleotide sequences to gain said co-localization information. The kit may also further comprise instructions for carrying out the methods of the invention and utilising the kit.

The kits of the invention may further comprise a protein display library wherein each member of said library is associated with a unique nucleotide sequence.

Comparison of the Methods of the Present Invention to Existing Methods

The method of the present invention is a novel approach to capture the information of the interactome in a time and cost effective manner, enabling random sampling and high redundancy of sampling. It provides dynamic, original cellular context based e.g. physiological, native protein-protein interaction based, and comprehensive coverage of quantitative interaction data of even large, multi-unit protein complexes. It suppresses the effects of random variables, such as detecting non-specific, accidentally interacting proteins. It, also, diminishes the effect of variables, such as any binding event related variables involved in the detection principle other than the original protein-protein interaction. The method is suitable for the in vitro detection of proteins that interact not only with the bait protein, but also with DNA, RNA and chemical compounds.

PCR based detection of a ligation proximity assay (LGA) is used to determine the relative expression of a target. As the protein and mRNA expression profiles are not identical, the differences observed could be significant with respect to biological processes. The assay is capable of detecting several targets in a given experiment. However as it is necessary to prepare a large number of specific antibodies which are artificially labelled, it is infeasible at the interactome level. Without highly specific antibodies, cross-reactivity reduces the ability of the proximity ligation assay to clearly distinguish specific and non-specific interactions. The parallel detection of targets at very large numbers becomes costly and cumbersome.

A multiplexed form of LGA has been developed. In this assay, an antibody immobilized on a solid support acts as a capture reagent to locally enrich an antigen from a complex mixture of proteins. After washing, a pair of proximity ligation assay (PLA) probes is added. This is followed by further washes and ligation of oligonucleotides brought in proximity. This enables higher specificity on the basis of the need for three binding events. This, in combination with the use of PCR amplification allows high specificity and sensitivity, and a broad dynamic range for protein quantification. This method coupled with next generation sequencing (NGS) to digitally record patterns of protein abundance, and be used to demonstrate simultaneous detection of 36 protein analytes.

A variation of LGA is described as an extremely sensitive and specific assay (4PLA) for detection of complex target structures such as microvesicles in which the target is first captured via an immobilized antibody and subsequently detected by using four other antibodies with attached DNA strands. The requirement for coincident binding by five antibodies to generate an amplifiable reporter results in both increased specificity and sensitivity.

All proximity ligation based assay types which use close proximity, need experimental validation due to very frequent steric constraints.

In the case of methods of invention, the low specificity is not an issue, and can even be used as validation information. The methods of invention use co-localization and compartmentalization, wherein the amplified identity labels freely diffuse in compartments enabling more relaxed steric conditions.

Dual Expression Recombinase Based (DERB) destiny vectors individually encode two sets of recombinase recognizable sequences for inserting the protein open reading frame (ORF) of interest, two sets of promoters and reporter tags in frame with the ORFs for detecting interactions. Introduction of the vectors into living cells (prokaryotic and eukaryotic) enables the detection of protein interactions by fluorescence resonance energy transfer (FRET) or bimolecular fluorescence complementation (BiFC). The DERB platform shows advantages over current commercialized systems by introducing recombinase based cloning and compatible accepting vectors validated through proof-of-principle experiments and the identification of an unknown interaction. The system needs large numbers of screened interactions and consequently large efforts and cost, which suits only robotic systems at the interactome level and using artificial testing conditions (fusion proteins and artificial promoters).

The yeast two-hybrid (Y2H) screen is specific implementation of protein-fragment complementation assay, or PCA, where the identification of protein—protein interactions is based on two protein fragments, each covalently linked to incomplete fragments of a third protein (e.g. DHFR, which acts as a reporter). Interaction between the proteins brings the fragments of the reporter protein in close enough proximity to allow them to form a functional reporter protein whose activity can be measured. This principle can be applied to many different reporter proteins, as the yeast two-hybrid screen using GAL4 transcription factor. The yeast two-hybrid screen investigates the interaction between artificial fusion proteins inside the nucleus of yeast. The method has a high false-positive rate, which makes it necessary to verify the identified interactions by other means. The method is out of cellular context and the lack of natural environment limits its use for interactions governed by cellular context specific modifications of the protein or in the case of low affinity interactions. At the interactome level it requires further optimisation and the use of arrays, to make it possible to construct the very large interactome datasets. This involves high costs, but still do not overcome all the limitations of this assay type.

A dual bait system can be used which improves the accuracy of library screens with an immediate selection to eliminate false positives.

A coiled-coil mediated heterodimerization functional interaction trap assay has been described, where coiled-coil heterodimerization domains are substituted for modular protein binding domains. This can be useful for validating functionally relevant protein-protein interactions, directing enzymes to specific substrates, and screening fusion libraries for functionally important interaction partners.

In response to known limitations of Y2H screens, a mammalian cell based two hybrid (M2H) system was developed. This M2H system is similar to that of the yeast two-hybrid in that interactions are investigated by fusing each protein pair of interest to a DNA binding and a transcriptional trans-activation domain respectively. Mammalian cell based two-hybrid techniques have a number of advantages, compared to yeast based assays and solving some of the known issues. As yeasts lack key proteins involved in post-translational modifications, interaction based on these proteins cannot be assayed. Furthermore, several different mammalian cell contexts can be used to provide cellular context specific interactome data. However large datasets are difficult produce so interactome level of interactions cannot be achieved due to the necessity of handling very large number of mammalian cell culture specimens.

A variation of detecting protein-protein interactions in Y2H screens is to use a specific PCR based sequencing method, termed Stitch-seq. This is PCR stitching, which places a pair of sequences encoding interacting proteins on the same PCR amplicon. PCR stitching consists of two rounds of PCR. In the first round, X and Y (present on the Y2H DB-X and AD-Y vectors) are amplified with DB- and AD vector-specific upstream primers, respectively. Amplicons from the first round as templates used to produce a concatenated PCR product composed of X and Y ORFs connected by an 82-bp linker sequence. The PCR products are pooled and sequenced by next-generation DNA sequencing to produce stitched ISTs (sISTs). Stitch-seq has removed the bottleneck of some Y2H protocols, but still does not solve the problems associated with key steps.

A patent describing the following improvements to the PCA: 1) reporter genes (and methods for detecting their expression) that readily permit the analysis of large libraries ($>10^7$ in size) and whose selectivity can be easily "tuned," modified, and/or monitored, 2) methods for the simultaneous and independent measurement of multiple interactions (as judged by expression of different reporter genes), and 3) construction of libraries using a phagemid-based system that provides a) an efficient, automatable method for performing library vs. library experiments and b) a method to simplify the analysis of positive candidates from any screen/selection performed in the prokaryotic PCA. The use of this phagemid-based technology to screen library vs. library involves crossing libraries e.g. one infect the bait library of cells with the prey library of phage (using an excess of cells over phage to ensure that each cell is on average only infected by one phage) and look for activated expression of the reporter gene. This is significant step toward large scale interactome scans, however it is neither dynamic nor cellular context based.

For library vs. library experiments conducted in yeast, formation of a diploid a cell harbouring the DNA from both the starting haploid cells is used. Thus, cells harbouring a library of prey hybrids can be mated with a cells harbouring a test bait hybrids. Whilst this eliminates transformation efficiency issues, it does not address the other requirements of ideal interactome scans.

Two leucine zipper libraries, semi-randomized at the positions adjacent to the hydrophobic core, were genetically fused to either one of two designed fragments of the enzyme murine dihydrofolate reductase (mDHFR), and cotransformed into *E. coli*. Interaction between the library polypeptides was required for reconstitution of the enzymatic activity of mDHFR, allowing bacterial growth. This strategy however is limited by the transformation efficiency that can be achieved in bacterial cells.

The adaptation of a GST-pulldown assay to a 96-well filter plate format is also devised. The use of a multi-well filter plate makes it possible to assay more samples in significantly less time using less reagents and more efficient sample processing than does the traditional single tube assay. This assay type solved some of the problems causing technical bottlenecks; however it is infeasible to generate very large datasets required, using this system.

The Tandem affinity purification (TAP) method, can be seen as a more specific version of co-immunoprecipitation, allows the high-throughput identification of proteins interactions. The accuracy of the method can be compared to those of small-scale co-immunoprecipitation experiments and the interactions are detected within the correct cellular context. However, it requires two successive steps of protein purification, so cannot readily detect transient protein-protein interactions. The TAP method applies the fusion of the TAP tag to the C-terminus of the protein under study. The TAP tag consists of calmodulin binding peptide (CBP) from the N-terminal, followed by tobacco etch virus protease (TEV protease) cleavage site and Protein A. It is capable to provide the real determination of protein partners quantitatively in the correct cellular context, however the method, at the interactome level, requires large effort and would incur large costs to cover the entire proteome with the used constructs.

In response to this issue, the tagless strategy was developed to perform systematic, highly extensive biochemical fractionation of the soluble human protein interactome using multiple separation techniques including nondenaturing high-performance multibed ion-exchange chromatography, sucrose gradient centrifugation and isoelectric focusing. The method needs verification and statistical analysis to produce reliable datasets, also needs significant amount a sample material and its cost limits its usage for random sampling and high redundancy of sampling.

Protein microarrays have introduced a new approach to identify and characterize protein interactions, providing the ability to rapidly identify new interactions between thousands of proteins in a single experiment. Since the location and identity of each protein on the array is known, interaction maps can be developed rapidly from iterative probing of protein arrays. Because a protein microarray experiment is performed within a day, and interactions are assessed in the context of thousands of other proteins, interaction profiling on microarrays can greatly accelerate the rate at which novel protein interactions are discovered. Additionally, the in vitro nature of protein microarray experiments permits control over probing conditions that affect protein interactions such as protein concentration, post-translational modifications, and presence of cofactors, which may not be possible with other methods such as yeast two-hybrid screening. However, the classical one probe at a time approach is not suitable for large interactome level experiments.

A version of protein array based detection is used, where cellular protein lysate or synthetic peptide mixes is applied to the protein array with immobilized bait protein/peptide. The nonspecific proteins/peptides are washed off under various stringent conditions and only the proteins specifically interacting with the bait protein/peptide remain on the chip. Last, the captured interacting protein/peptide complexes are then analyzed by SELDI-TOF mass spectrometry and their identities are confirmed by their predicted distinctive masses. It is highly promising approach, however protein sequencing by SELDI-TOF is limited by several factors (amount of protein, separation, post-translational modifications) and the interactions lack the natural context.

The protein mixture can also be immobilised on a solid support, and contacted with a plurality of unlabelled protein-protein interaction domains under appropriate binding conditions. In the presence of at least one labelled selected protein-protein interaction domain, (the labelled protein-protein interaction domain being different from the unlabelled protein-protein interaction domains) the binding of the labelled protein-protein interaction domain is measured. This method is interaction domain specific, which limits its application.

A cell-free display technology combined with next generation sequencing (NGS) can improve both the coverage and reliability of interactome datasets. The completely cell-free method gives a high-throughput and a large detection space, testing the interactions without using clones. The quantitative information provided by NGS reduces the number of false positives. The method is suitable for the in vitro detection of proteins that interact not only with the bait protein, but also with DNA, RNA and chemical compounds. The method employs a complete in vitro treatment with cDNA libraries (extracted from cells and tissues) and selection on target proteins to gain selected cDNA sequences for NGS. Selections using the method are conducted under cell-free conditions, and subsequent sequencing by NGS is not limited by cloning steps using any kind of cells. This method applies one at time approach in out of cellular context, which limits its ability to generate large datasets at the interactome level.

Another cell free assay utilizes the so-called inteins, which are peptide sequences capable of directing protein trans-splicing in vitro. An intein is an intervening protein sequence in a protein precursor that is excised from the protein precursor during protein splicing. Two hybrid fusion constructs are provided, where one has a first test agent and an N-terminal intein fragment or N-intein, and the other has a second test agent and a C-terminal intein fragment or C-intein. In addition, one or both fusion constructs may have a reporter that undergoes detectable changes upon trans-splicing of the fusion constructs. Both the throughput and the cellular context free features are significant disadvantages of this method.

Another method used to study protein-DNA or protein-protein interactions is the method of phage display. Proteins are displayed on the surface of filamentous bacteriophage (e.g. M13) encoding DNA of the displayed protein. Target proteins or DNA sequences of interest are immobilized on a solid support and used to affinity-enrich libraries of phage-displayed proteins for candidates that bind to the target. The method has been used to identify and characterize both protein-DNA and protein-protein interactions. Phage display is an enrichment process that requires multiple cycles to infer protein-protein interaction data. The enrichments are performed in vitro, which biases the interactions and favour high affinity interaction in detection. Certain proteins (particularly larger ones) are not well suited for analysis by phage display. A major disadvantage of bacterium-based ORF phage display is that proteins displayed on phage surface lack appropriate post-translational modifications, such as glycosylation.

Phage display, as used in the art, is limited to reproducing natural binding events, as described above. However antibody repertoires expressed as phage display are extremely successful at providing pharmacological leads for therapeutic antibodies or detection antibodies for diagnostic assays. The present invention applied the phage display technology in the latter context, where the extremely large phage antibody libraries contain plurality of specificities covering almost any identifiable targets.

A variation of the phage display relates to a method for the selection and identification of interaction partners. Target molecules (ligands) are immobilized on the surface of a solid phase carrier such that they are position addressable in a two-dimensional grade and contacted to protein display viruses. The interaction partner is identified by detection and determination of the position of the binding between the immobilized ligand and the interaction partner. The preferred detection method described is surface plasmon resonance (SPR).

Chemical crosslinking is often used to "fix" protein interactions in place before trying to isolate/identify interacting proteins. Common cross-linkers for this application include the non-cleavable [NHS-ester] cross-linker, [bis-sulfosuccinimidyl suberate] (BS3); a cleavable version of BS3, [dithiobis(sulfosuccinimidyl propionate)](DTSSP);

and the [imidoester] crosslinker [dimethyl dithiobispropionimidate] (DTBP) that is popular for fixing interactions in ChIP assays.

A technology has been developed for identifying proteins that specifically bind predicted transcriptional regulatory elements using phage-display library of genomically encoded peptides, which bind to a surface immobilized double-stranded DNA, containing a DNA motif sequence of interest. After enrichment for a specific DNA-protein interaction, the bound phages are amplified, and the inserts from the enriched phage are sequenced to determine the interacting proteins using labelling and hybridization to DNA microarray.

One or more analytes have been reportedly measured using a chemFET array. The array may include any of a variety of chemical substances that provide relevant information regarding a chemical process or chemical processes of interest including binding of an antibody to an antigen. In some aspects, the ability to measure levels or concentrations of one or more analytes, in addition to merely detecting the presence of an analyte, provides valuable information in connection with the chemical process or processes.

As is apparent from the above description, the present invention provides a powerful, versatile, in vitro system for detecting and characterizing protein-protein interactions, and for selecting compounds capable of modulating protein-protein interactions. The system can be used with great convenience and can be easily adapted to high-throughput screening procedures.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practised within the scope of the appended claims.

Example 1

Phage lysis and detection in droplet digital PCR pBluescript II SK(+) phagemid vector (Agilent, 212205) f1 origin in (+) orientation, Sac->Kpn polylinker orientation in host strain: XL1-Blue MRF' have been used to generate pBluescript II SK(+) phage and M13KO7 Helper Phage (NEB, N0315S) was purchased. The phages were titrated to determine the number of infective phages. The phages were diluted serially by factor of 10 to achieve lower than single phage per compartment dilution. The dilutions was subjected to digital PCR using QX200 Droplet Digital PCR (ddPCR™) System. Briefly 5' CTCAAGTCGGTGACGGT-GAT 3' (M13KO7 specific forward (SEQ ID NO: 1)), 5' GACAAAAGGGCGACATTCAA 3' (M13KO7 specific reverse (SEQ ID NO: 2)) and/or 5' TCTT-GATCCGGCAAACAAAC 3' (pBluescript II SK(+) specific forward (SEQ ID NO: 3)), 5' TTTTCTGCGCGTAATCTGCT 3' (pBluescript II SK(+) specific reverse (SEQ ID NO: 4)) with the probes 5' CTGGTAGCGGTGGTTTTT 3' (pBluescript II SK(+) specific probe FAM-MGB labeled (SEQ ID NO: 5)), 5' CCGT-CAATATTTACCTTCCC 3' (M13KO7 specific probe VIC-MGB labeled (SEQ ID NO: 6)) were used to amplify the compartmentalized phages, the amplification were recorded in two different channels and the droplet generation, PCR and detection were according to the manufacturer protocol.

Effective phage lysis and single phage detection Poisson distribution of counts is detected indicating single phage detection sensitivity.

Example 2

Dimerisation PCR pBluescript II SK(+) phagemid vector (Agilent, 212205) f1 origin in (+) orientation, Sac->Kpn polylinker orientation in host strain: XL1-Blue MRF' have been used to generate pBluescript II SK(+) phage and M13KO7 Helper Phage (NEB, N0315S) was purchased. Phages was labeled with 20 molar excess of biotin according to the manufacturer instruction using EZ-Link Sulfo-NHS-Biotin (Thermo, 21326) and precipitated using isoelectric point precipitation as described (Dong D, Sutaria S, Hwangbo J Y, Chen P. A simple and rapid method to isolate purer M13 phage by isoelectric precipitation. Appl Microbiol Biotechnol. 2013 September; 97(18):8023-9.). Equal number of purified phages were mixed providing a concentration of 10e+6/ml of phages and have been combined with avidin (A9275-1MG, Sigma-Aldrich) in molar equivalence or used as a mixture and was subjected to digital PCR (QX200 Droplet Digital PCR (ddPCR™) System). Briefly 5' TAACGTGG-GAATGGTGCTTCCTCAAGTCGGTGACGGTGAT 3' (M13KO7 specific forward (SEQ ID NO: 7)), 5' GACAAAAGGGCGACATTCAA 3' (M13KO7 specific reverse (SEQ ID NO: 8)) and 5' GAAGCACCATTCC-CACGTTATCTTGATCCGGCAAACAAAC 3' (pBluescript II SK(+) specific forward (SEQ ID NO: 9)), 5' TTTTCTGCGCGTAATCTGCT 3' (pBluescript II SK(+) specific reverse (SEQ ID NO: 10)) with the probes 5'CTGGTAGCGGTGGTTTTT3' (pBluescript II SK(+) specific probe FAM-MGB labeled (SEQ ID NO: 11)), 5' CCGT-CAATATTTACCTTCCC 3' (M13KO7 specific probe VIC-MGB labeled (SEQ ID NO: 12)) were used to amplify the compartmentalized phages, the amplification were recorded in two different channels and droplet generation, PCR and detection were according to the manufacturer protocol. Increased "linkage" counts were expected in the presence of avidin due to biotin-avidin binding. To detect dimerised PCR products the amplified DNA was extracted according to the manufacturer recommendation and subjected to PCR using primers 5' TTTTCTGCGCGTAATCTGCT 3' (pBluescript II SK(+) specific reverse (SEQ ID NO: 13)), 5' GACAAAAGGGCGACATTCAA 3' (M13KO7 specific reverse (SEQ ID NO: 14)) and probes 5' CTGGTAGCGGTGGTTTTT 3' (pBluescript II SK(+) specific probe FAM-MGB labeled (SEQ ID NO: 15)), 5' CCGT-CAATATTTACCTTCCC 3' (M13KO7 specific probe VIC-MGB labeled (SEQ ID NO: 16)) in real-time PCR instrument. Only the correctly dimerised products are amplifiable and the expected amplification signal is generated by both probes.

Example 3

Compartment Based Identification of Proteins/Protein Complexes (a) Extraction of protein complexes is achieved by standard means—including any separation method, which provides even partially preserved protein complexes and methods to partially purify protein complexes (e.g. according to their post-translational modification or other).

(b) Antibody library phages are combined with the protein complexes and are diluted and compartmentalized to achieve single phage level of separation for unbound phages. The compartmentalization (e.g. effective separation of large number reactions) is based on the Poisson distribution based separation of single unbound phages; e.g. emulsions and microarray are the best known state-of-art method. The only requirements are the minimal unspecific co-localization with phages and protein complexes. The nucleotide sequences are linked using effective heat lysis of phages followed by linking PCR process.
(c) The antibody encoding (based on any CDR regions of antibody gene in the phage library, preferably CDR3 based), specific DNA fragments of phages (bound and unbound) per compartment are amplified (using dimerisation capable general primers) and linked (dimerisation PCR for an example see Example 2 and 4.)
(d) The generated dimerised, even unpurified PCR amplicons are preferably combined using DNA extraction from the emulsion or physical removal the reactions from the microarray cavities or other means.
(e) The linkage information of the multitude of PCR dimer amplicons is revealed in a highly parallel and quantitative manner preferably by next generation DNA sequencing.
(f) The predetermined binding characteristics information of individual phages (see Example 5 and 7.) and the linkage information of bound phages is used to compute the interactome on statistical basis including determination of significant interactions on the basis of background subtracted linkage information (removal of promiscuous or random or incidental interactions); confirmation and filtration of interaction on the basis of redundant linkage information of different phages with the same binding characteristics information possibly weighted by their known dissociation constant information; determination of dimer and multi-mer interactions on the basis of confirmed and filtered, possibly weighted linkage information; measurement of relative abundance of proteins and protein complexes on the basis of quantitative linkage information; confirmation, calculation of statistical error of determination of dimer and multi-mer interactions and the relative abundance of proteins and protein complexes on the basis of redundant measurements of the detection of several phages with the same binding characteristics information Example 4

Compartment Based Identification of Control Proteins/Protein Complexes

Antibody displaying M13 phages were purchased from Source BioScience (6001_hDAb) including a phagemid antibody library (~3×10 9) (Dudgeon K, Famm K, Christ D. Sequence determinants of protein aggregation in human VH domains. Protein Eng Des Sel. 2008 Oct. 28.) KM13 helper phage, TG1Tr bacterial strain and anti-beta-galactosidase & anti-bovine ubiquitin antibodies display phages. The control phages were sequenced by NGS (ThermoFisher Scientific PGM, Ion Xpress™ Plus Fragment Library Kit, 4471269) and their binding affinities were verified by ELISA against the respective antigens. The antigens are the mono-biotinylated ubiquitin (b-UBI) from LifeSensors (#S1280), beta-galactosidase biotin labeled (G5025) (b-BGAL). Avidin from egg white (A9275) is also from Sigma-Aldrich.

On the basis of sequencing results general primers are designed: general forward—CCAAGAACACGCTGT-ATCTGCA (SEQ ID NO: 17); dimerisation capable general reverse primers—TGCGCATCCATTGTAGAGGTGA-GACGGTGACCAGGGTTCC (SEQ ID NO: 18) and ACCTCTACAATGGATGCGCAGAGACGGTGACC-AGGGTTCC (SEQ ID NO: 19). To detect dimerised products a dimer specific real-time PCR reaction is designed: forward—AGTTGGAGTCTTGGGGTCAGG (SEQ ID NO: 20), reverse—AGGTGGGTCGATGTTTGACTACTG (SEQ ID NO: 21) and probe—FAM TCTCACCTCTA-CAATGGAT MGB (SEQ ID NO: 22).

Control phage specific probes are also designed: anti-beta-galactosidase—FAM GCTAGGGCTATGTATCC MGB (SEQ ID NO: 23); anti-bovine ubiquitin—VIC TGGGTCGATGTTTGACTAC MGB (SEQ ID NO: 24).

According to the instructions control phages are amplified (anti-beta-galactosidase $3.8\times10^{12}$/ml=6.48 nM, anti-bovine ubiquitin $4.0\times10^{12}$/ml=6.7 nM)). Avidin (36 nM) (or it was omitted), b-UBI (72 nM) and b-BGAL (72 nM for the monomer) were combined and incubated for one hour at room temperature to form complexes. The ten times diluted complexes were combined and incubated overnight with control phages at 1.5 nM. The phage bound complexes are diluted 2×106 times and according to the protocol of (QX200 Droplet Digital PCR (ddPCR™) System) emulsion droplets are generated and amplified using PCR conditions: ddPCR Supermix for Probes (no dUTP) (186-3023), general forward primer concentration is 800 nM, dimerisation capable general reverse primers concentration is 50 nM. In some cases control phage specific probes are also added at 250 nM. The amplified droplets are chloroform extracted according to the manufacturer protocol to recover amplified dimer products.

The dimers are successfully detected by the dimer specific real-time PCR proving their correct dimerised structure. Increased 'linkage'-es were detected in the presence of avidin due to control phages and the avidin/antigen complex binding if the control specific probes were included in the emulsion PCR reaction, indicating detection of anti-beta-galactosidase and anti-bovine ubiquitin phages were localized at the same droplet at a higher rate than only by chance.

Example 5

Predetermining the binding characteristics information of an antibody phage library
(a) Antibody (the phage library, which binding characteristics information to be determined) and cDNA library phages (constituting of those cDNAs, which against the binding characteristics information of an antibody phage library will be determined) are combined and the antibody-cDNA phage complexes are diluted and compartmentalized to achieve single phage level of separation for unbound phages—for further details see Example 3. part (b),
(b) The antibody encoding (based on any CDR regions of antibody gene in the phage library, preferably CDR3 based) and the cDNA encoding (the cDNA fragment) DNA sequences of phages (bound and unbound) per compartment are amplified (using dimerisation capable general primers) and linked (dimerisation PCR as an example see Example 2. and 4.)
(c) The generated dimerised PCR amplicons are preferably combined using DNA extraction from the emulsion or physical removal the reactions from microarray cavities (d) The linkage information of the multitude of PCR dimer amplicons is revealed in a highly parallel and quantitative manner preferably by next generation DNA sequencing.

(e) The linkage information of bound phages is used to compute the binding characteristics information of the antibody phage library against the cDNA-phage library including determination of significant interactions on the basis of background subtracted linkage information (removal of promiscuous or random or incidental interactions); identification of significant antibody—cDNA bindings on the basis of statistically significant interactions; determination of the binding characteristics information for each detected antibody-phages including detected cDNA fragments, inferred detected proteins; confirmation, calculation of statistical error of the binding characteristics information on the basis of redundant measurements of the detection of several phages with the same binding characteristics information.

Example 6

Enrichment of an Antibody Phage Library
(a) cDNA library phages (constituting of those cDNAs, which need to be detected by the enriched antibody phage library) are immobilized by separable means (for the separation of unbound antibody phages), preferably on microbeads
(b) Antibody library phages (the phage library, which enrichment is intended) are combined with immobilized cDNA-phages to achieve the separation of bound and unbound phages
(c) Unbound antibody phages are removed, preferably by washing
(d) Bound antibody phages are eluted and optionally amplified by suitable means to get a high titer preparation
(e) Optionally the high titer preparation of enriched antibody phages are subjected to next round of enrichment
(f) Optionally the eluted bound phages are verified against the cDNA phage library using the method described in Example 5.

Example 7

Predetermining the Binding Characteristics Information of an Enriched Antibody Phage Library Antibody displaying M13 phages were purchased from Source BioScience (6001_hDAb) including a phagemid antibody library (~3×10 9) (Dudgeon K, Famm K, Christ D. Sequence determinants of protein aggregation in human VH domains. Protein Eng Des Sel. 2008 Oct. 28.) KM13 helper phage and TG1Tr bacterial strain. The library was amplified, infected with KM13 helper phage and the phages were harvested according to the protocol (Lee C M, Iorno N, Sierro F, Christ D. Selection of human antibody fragments by phage display. Nat Protoc. 2007; 2(11):3001-8.). PhD12 Phage Display Peptide Library (E8110S) and *E. coli* ER2738 host strain was purchased from New England Biolabs. The PhD12 library was plagued on LB/IPTG/Xgal plates and 50 plaques were picked and combined (antigen bait library). The antigen bait library was absorbed on microtiter plate and the panning was carried out using the full Source BioScience (6001_hDAb) library according to the Source BioScience (6001_hDAb) library protocol. Altogether 612 clones were plated out on LB/ampicillin plates, which were amplified, infected with KM13 helper phage and harvested (enriched antibody library).

On the basis of sequences of the phages general primers are designed: general forward Source BioScience (6001_hDAb) library specific—CCAAGAACACG-CTGTATCTGCA (SEQ ID NO: 25); dimerisation capable general reverse primer Source BioScience (6001_hDAb) library specific—TGCGCATCCATTGTAGAGGTGA-GACGGTGACCAGGGTTCC (SEQ ID NO: 26) and general forward PhD12 Phage Display Peptide Library specific—CGCAATTCCTTTAGTGGTACCTTT (SEQ ID NO: 27); dimerisation capable general reverse primer PhD12 Phage Display Peptide Library specific—ACCTCTA-CAATGGATGCGCATCTGTATGGGATTTTGCTAAA-CAACT (SEQ ID NO: 28).

To detect dimerised products a dimer specific real-time PCR reaction is designed: forward—CGGACTGTT-GAAAGTTGTTTAGCA (SEQ ID NO: 29), reverse—GGT-CACCGTCTCACCTCTAC (SEQ ID NO: 30) and probe—VIC-CATACAGATGCGCATCC-MGB (SEQ ID NO: 31).

The $10^{12}$ antigen bait library and enriched antibody library phages were combined and incubated overnight at room temperature. The phage complexes are diluted $2\times10^6$ times and according to the protocol of (QX200 Droplet Digital PCR (ddPCR™) System) emulsion droplets are generated and amplified using PCR conditions: ddPCR Supermix for Probes (no dUTP) (186-3023), general forward primer concentration is 800 nM, dimerisation capable general reverse primers concentration is 50 nM. The amplified droplets are chloroform extracted according to the manufacturer protocol to recover amplified dimer products. The amplified dimer products are NGS sequenced and specific bait library and enriched antibody library dimerised products are detected indicating specific sequenced based interactions between the members of the antigen bait library and hedged antibody library.

Example 8

Determining the Quantitative Binding Information of the Members of an Antibody Phage Library
(a) applying the method in Example 3. with a modification that in step b., several quantified amount of protein complexes are used at equilibrium conditions resulting in several parallel determinations
(b) On the basis of the quantitative information gained in the parallel determinations, quantitative binding curves can be constructed for a multitude of protein-phage interactions and dissociation constant and binding capacity information can be calculated.

Example 9

Stoichiometry of Invention

Regarding binding stoichiometry 1 nM of protein in the cell volume of *E. coli* is approximately 1 molecule/cell and 2,000 molecules/mammalian (HeLa) cell, and the characteristic concentration for a signalling proteins (as an example here) are in the range 10 nM-1 microM. Moreover as the dissociation constant (Kd) of phage display antibodies is in the range of 10 nM and down to 0.1 nM and off-rates of $10^{(-3)}$ to $10^{(-4)}$ s$^{-1}$ and as these phages can be routinely selected, saturation binding stoichiometry is expected for most proteins/epitopes and off-rates provide enough time to compartmentalise complexes without early dissociation.

There are $2-4\times10^6$ proteins per cubic micron (i.e. 1 fL) in bacteria, yeast, and mammalian cells (Bioessays. 2013 December; 35(12):1050-5.) for the volume of 5000 eukaryotic cells (10000 fL) it is $10^{10}$ proteins and the maximum phage concentration is around $10^{16}$/ml→in 10000 fL volume: $10^{11}$ phages.

The interactome complexity in the range of 10(+4-5), desired interaction/phage multiplexity is about 10, which corresponds $10^5$ individual phages Furthermore i.e. 0.1 nM per individual phage (at $10^{16}$/ml), and as every protein of more than $10^6$ per 10000 fL (0.01% of total protein) has a concentration of larger than 1 nM and the average 0.1-1 nM Kd of an antibody phage (HuCAL GOLD subnanomolar probability: 30%) (J. Mol. Biol. (2008) 376, 1182-1200) can provide a saturation of 50-5%. This is corresponding to the co-localised saturation of 25-0.25% (co-localised saturation means that two bound phages with distinct specificities are localised in the same compartment).

In the case of HiSEQ 2500 NGS instrument at 0.25% of co-localisation rate the 300 million reads (10-300 Gb, 250 bp reads) corresponds the minimum number of heterodimeric PCR products of $7 \times 10^5$, which means a minimum binary interaction sequencing coverage: 375.

A fully randomised, primary, high coverage antibody phage library complexity are up to $10^{(+13)}$ of individual phage clones and the number of manageable emulsion PCR or microarray compartments are in the range of $10^5$-$10^8$ (the current number of a NGS chip compartments), these disproportional numbers need to be merged by reducing the complexity of antibody phage libraries and increase the abundance of phages with binding capacity against targeted proteins (targeting partial or full interactome), To reduce complexity a specific selection process is devised—selecting phages from fully randomised libraries using library (antibody) selection against library (cDNA) method results in low complexity, affinity enriched, naïve, general purpose phage library, moreover the process can be monitored by detecting the antibody-protein bindings during the selection process or even binding kinetics information can be extracted using for example different amount of input protein display phages.

It is also possible to generate libraries by gradual construction of more and more complex libraries using bottom-up (mixing phages with known binding characteristics and adding background phages; these are specific libraries tailored to specific tasks, and top-down approaches (e.g. by reducing complexity by selecting the interacting phages)

Example 10

Statistical Evaluation of the Information Gained
(a) Extraction of protein complexes is achieved by standard means, and antibody library phages are combined and the formed complexes are diluted and compartmentalised to achieve single phage level of separation for unbound phages.
(b) The antibody encoding, specific DNA fragments of phages (bound and unbound) per compartment are amplified and linked together by PCR (preferably by limited number of amplication cycles).
(c) This linkage information is revealed in a highly parallel and quantitative manner by next generation DNA sequencing.
(d) The predetermined binding characteristics information of individual phages and the linkage information of bound phages is used to compute the interactome.

The method is based on the compartment based identification of proteins/protein complexes, in which protein-antibody identities of a single protein complex per compartment translated to DNA. The identification of all linked DNA fragments are used to quantitatively determine the interactions, however unbound phages accidentally trapped in the same compartment can contribute to a background. This background can handled by simple statistical means as it is a random event, which can be differentiated from specific events. The distribution of binding agents during compartmentalisation is governed by Poisson distribution, thus counting the occurrences of each binding agents (by the determination of their relative abundances of binding agents by NGS after limited compartment based PCR amplification), if the number of compartments are known, thus the background detection of proteins/protein complexes can be calculated. A multitude of specific binding events will be used to identify the exact target proteins of the antibodies as in multi-protein complexes linkage information is due to the co-localisation, and indicates direct binding. As for each proteins/protein complexes the background detection is calculated any variation of detection of proteins/protein complexes is due to real binding effects, which can be calculated by simple subtraction by removing the calculated background detection of proteins/protein complexes (or Poisson corrected subtraction as proteins/protein complexes bound binding agents change the overall number of binding agents). If varied combinations, at equilibrium conditions, of the reacting antibody and protein analytes are used Scatchard plot or other binding kinetics calculations can be constructed to calculate the Kds or other parameters for the antibody protein interactions. The interactome internal kinetics data for all or several interactions also can be calculated using different concentration of the interacting proteins (changing the experimental conditions or using spiked analysis).

The invention claimed is:

1. A method of determining a binding interaction between a binding agent and a target comprising
   a) contacting a binding agent library with a target to allow formation of binding agent/target complex, wherein each member of said binding agent library is associated with a unique nucleotide sequence and wherein said target is associated with a unique nucleotide sequence;
   b) isolating said binding agent/target complexes into compartments so that there is a single binding/agent complex in one compartment;
   c) linking the unique nucleotide sequence(s) associated with the binding agent and target in the binding agent/target complex to form a linked nucleotide sequence, wherein isolation of the isolated binding agent/target complexes is maintained during the linking step;
   d) identifying the binding agent(s) present in the complex from the linked nucleotide sequence; and
   e) using the linked nucleotide sequence correlating the unique nucleotide sequence of each member of said binding agent library with the binding characteristics of said member.

2. The method as claimed in claim 1 wherein said binding agent library comprises an antibody library.

3. The method of claim 2 wherein said antibody library comprises an antibody display library or a library of antibodies wherein each antibody is labelled with said unique nucleotide sequence.

4. The method of claim 1 wherein said target comprises a protein.

5. The method of claim 1 wherein said target comprises a Protein display library, herein each member of said library is associated with a unique nucleotide sequence.

6. The method of claim 4, wherein said protein is within a protein mixture or an enriched protein mixture.

7. The method of claim 6, wherein said protein mixture is enriched for phosphoproteins, membrane proteins, and/or naturally or artificially modified proteins.

8. The method of claim 1 wherein binding agents which bind to other binding agents are removed from the binding agent library prior to use.

9. The method of claim 1 wherein the binding agent library is enriched prior to use.

10. The method of claim 1 wherein said compartment is on a solid surface.

11. The method of claim 1 wherein said compartment is an emulsion droplet, diffusion limited or separated compartment.

12. The method of claim 1 wherein the nucleotide sequence associated with binding agent in the complex is joined to another nucleotide sequence associated with a binding agent in the complex or joined to the nucleotide sequence associated with the target within the binding agent/target complex.

13. The method of claim 1 wherein the (i) binding agent or (ii) binding agent and target present within the complex are identified by sequencing said linked nucleotide sequence.

14. The method of claim 1 wherein said binding agent/target complex is immobilized following isolation.

15. The method of claim 1 wherein linked nucleotide sequences from more than one complex are combined prior to identifying the binding agent and/or target present.

16. The method of claim 1 wherein step (a) of contacting the binding agent library with a target is carried out in the presence or absence of a compound.

17. The method of claim 1 wherein joining the nucleotide sequences comprises:
   i. amplifying the nucleotide sequence associated with the binding agent or binding agent and target using at least two pairs of PCR primers to produce at least two sets of amplicons, wherein the primers are designed so that the amplicons generated by a first set of primers comprise a sequence which is complementary to a sequence in the amplicons generated by the second set of primers;
   ii. annealing the sets of amplicons;
   iii. carrying out an amplification reaction to produce a linked nucleotide sequence.

18. The method of claim 17 wherein steps i-iii are carried out concurrently.

19. The method of claim 1 wherein the method is repeated and the concentration of the target or binding agent library is varied.

* * * * *